US010101581B2

(12) United States Patent
Pugh et al.

(10) Patent No.: US 10,101,581 B2
(45) Date of Patent: Oct. 16, 2018

(54) ELECTRONIC OPHTHALMIC LENS WITH EYE CLOSED SENSOR WITH OPEN EYE PROMPT AND DATA LOGGING

(71) Applicant: Johnson & Johnson Vision Care, Inc., Jacksonville, FL (US)

(72) Inventors: Randall B. Pugh, St. Johns, FL (US); Adam Toner, Jacksonville, FL (US)

(73) Assignee: Johnson & Johnson Vision Care, Inc., Jacksonville, FL (US)

(*) Notice: Subject to any disclaimer, the term of this patent is extended or adjusted under 35 U.S.C. 154(b) by 0 days.

(21) Appl. No.: 14/810,669

(22) Filed: Jul. 28, 2015

(65) Prior Publication Data

US 2017/0031159 A1 Feb. 2, 2017

(51) Int. Cl.
| | |
|---|---|
| *A61F 2/16* | (2006.01) |
| *G02B 27/00* | (2006.01) |
| *G02C 7/02* | (2006.01) |
| *G02C 7/04* | (2006.01) |
| *G02C 11/00* | (2006.01) |
| *G08B 21/06* | (2006.01) |

(Continued)

(52) U.S. Cl.
CPC ............ *G02B 27/0093* (2013.01); *A61B 3/10* (2013.01); *A61B 5/18* (2013.01); *A61B 5/4809* (2013.01); *A61B 5/6821* (2013.01); *A61F 2/16* (2013.01); *A61F 2/1613* (2013.01); *G02C 7/04* (2013.01); *G02C 11/10* (2013.01); *G08B 21/06* (2013.01); *A61F 2002/1699* (2015.04); *A61F 2250/008* (2013.01); *A61F 2250/0091* (2013.01)

(58) Field of Classification Search
CPC ................. A61F 2/16; A61F 2250/008; A61F 2002/768; G08B 21/06; G02B 27/0093; G02C 7/04
See application file for complete search history.

(56) References Cited

U.S. PATENT DOCUMENTS

| | | | | |
|---|---|---|---|---|
| 6,087,941 A | * | 7/2000 | Ferraz | G08B 21/06 340/575 |
| 7,527,375 B2 | * | 5/2009 | Blum | G02C 7/08 351/141 |

(Continued)

FOREIGN PATENT DOCUMENTS

| | | |
|---|---|---|
| EP | 2772789 A1 | 9/2014 |
| EP | 2846182 A2 | 3/2015 |
| WO | WO2002067688 A1 | 9/2002 |

OTHER PUBLICATIONS

Dr. Andrew Tucker, "In the Blink of an Eye", www.optalert.com, Jan. 2014.

(Continued)

*Primary Examiner* — Dinah Baria

(57) ABSTRACT

An eyelid position sensor system for an ophthalmic lens comprising an electronic system is described herein for determining at least one of drowsiness or sleep onset of the wearer. The eyelid position sensor system is part of an electronic system incorporated into the ophthalmic lens. The electronic system in at least one embodiment includes a power source, power management circuitry, one or more sensors, clock generation circuitry, control algorithms and circuitry, and an alert mechanism. The eyelid position sensor system is utilized to determine eyelid position and use this information to determine if the wearer is asleep or awake.

17 Claims, 21 Drawing Sheets

(51) Int. Cl.
*A61B 3/10* (2006.01)
*A61B 5/18* (2006.01)
*A61B 5/00* (2006.01)

(56) References Cited

U.S. PATENT DOCUMENTS

| | | | |
|---|---|---|---|
| 2003/0021601 A1 | 1/2003 | Goldstein | |
| 2003/0139687 A1 | 7/2003 | Abreu | |
| 2012/0140167 A1* | 6/2012 | Blum | A61F 2/1624 351/159.34 |
| 2013/0258287 A1* | 10/2013 | Pugh | A61B 5/1103 351/210 |
| 2013/0261743 A1* | 10/2013 | Humphreys | G02C 7/04 623/6.11 |
| 2014/0081178 A1* | 3/2014 | Pletcher | G02C 7/04 600/595 |
| 2014/0148899 A1* | 5/2014 | Fehr | A61F 2/1624 623/6.22 |
| 2014/0240655 A1 | 8/2014 | Pugh | |
| 2014/0243645 A1* | 8/2014 | Leonardi | A61B 3/16 600/398 |
| 2014/0267141 A1* | 9/2014 | Yilmaz | G06F 3/044 345/174 |
| 2015/0061990 A1 | 3/2015 | Toner | |

OTHER PUBLICATIONS

Dr. Andrew Tucker, "Measuring Drowsiness with the JDS", www.optalert.com, Aug. 2014.

Johns MW, Epworth Sleep Centre, Melbourne, Australia, "Eyelid Closure, Visual Suppression and Hypovigilance in the Drowsy State: Lapses in Performance with Eyes Open or Closed", www.mwjohns.com.

Vanessa E. Wilkinson, Ph.D, et al., "The Accuracy of Eyelid Movement Parameters for Drowsiness Detection", Journal of Clinical Sleep Medicine, vol. 9, No. 12, 2013.

* cited by examiner

ELECTRONIC OPHTHALMIC LENS WITH EYE CLOSED SENSOR WITH OPEN EYE PROMPT AND DATA LOGGING

BACKGROUND OF THE INVENTION

1. Field of the Invention

The present invention relates to a powered or electronic ophthalmic lens, and more particularly, to a powered or electronic ophthalmic lens having a sensor and associated hardware and software for detecting eyelid position.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance performance of the eye. In another example, either with or without adjustable focus, a wearable contact lens may incorporate electronic sensors to detect concentrations of particular chemicals in the precorneal (tear) film. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

The human eye has the ability to discern millions of colors, adjust easily to shifting light conditions, and transmit signals or information to the brain at a rate exceeding that of a high-speed internet connection. Lenses, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Contact lenses may be utilized to correct myopia, hyperopia, astigmatism as well as other visual acuity defects. Contact lenses may also be utilized to enhance the natural appearance of the wearer's eyes. Contact lenses or "contacts" are simply lenses placed on the anterior surface of the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeability and are generally more comfortable to wear than the contact lenses made of the earlier hard materials.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered ophthalmic lenses may be designed to provide enhanced vision via zoom-in and zoom-out capabilities, or just simply modifying the refractive capabilities of the lenses. Electronic and/or powered contact lenses may be designed to enhance color and resolution, to display textual information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, and provide novelty image displays. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This, coupled with a wireless data transmitter, could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The proper combination of devices could yield potentially unlimited functionality; however, there are a number of difficulties associated with the incorporation of extra components on a piece of optical-grade polymer. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters of a transparent polymer while protecting the components from the liquid environment on the eye. It is also difficult to make a contact lens comfortable and safe for the wearer with the added thickness of additional components.

Given the area and volume constraints of an ophthalmic device such as a contact lens, and the environment in which it is to be utilized, the physical realization of the device must overcome a number of problems, including mounting and interconnecting a number of electronic components on a non-planar surface, the bulk of which comprises optic plastic. Accordingly, there exists a need for providing a mechanically and electrically robust electronic contact lens.

As these are powered lenses, energy or more particularly current consumption, to run the electronics is a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption, for example, up to eighteen (18) hours on a single charge, after potentially remaining idle for years. Accordingly, there exists a need for a system that is optimized for low cost, long-term reliable service, safety and size while providing the required power.

In addition, because of the complexity of the functionality associated with a powered lens and the high level of interaction between all of the components comprising a powered lens, there is a need to coordinate and control the overall operation of the electronics and optics comprising a powered ophthalmic lens. Accordingly, there is a need for a system to control the operation of all of the other components that is safe, low-cost, and reliable, has a low rate of power consumption and is scalable for incorporation into an ophthalmic lens.

Powered or electronic ophthalmic lenses may have to account for certain unique physiological functions from the individual utilizing the powered or electronic ophthalmic lens. More specifically, powered lenses may have to account for blinking, including the number of blinks in a given time period, the duration of a blink, the time between blinks and any number of possible blink patterns, for example, if the individual is dosing off. Blink detection may also be utilized to provide certain functionality, for example, blinking may be utilized as a means to control one or more aspects of a powered ophthalmic lens. Additionally, external factors, such as changes in light intensity levels, and the amount of visible light that a person's eyelid blocks out, have to be accounted for when determining blinks. For example, if a room has an illumination level between fifty-four (54) and one hundred sixty-one (161) lux, a photosensor should be sensitive enough to detect light intensity changes that occur when a person blinks.

Ambient light sensors or photosensors are utilized in many systems and products, for example, on televisions to adjust brightness according to the room light, on lights to switch on at dusk, and on phones to adjust the screen brightness. However, these currently utilized sensor systems are not small enough and/or do not have low enough power consumption for incorporation into contact lenses.

It is also important to note that different types of blink detectors may be implemented with computer vision systems directed at one's eye(s), for example, a camera digitized to a computer. Software running on the computer can recognize visual patterns such as the eye open and closed. These systems may be utilized in ophthalmic clinical settings for diagnostic purposes and studies. Unlike the above described detectors and systems, these systems are intended for off-eye use and to look at rather than look away from the eye. Although these systems are not small enough to be incorporated into contact lenses, the software utilized may be similar to the software that would work in conjunction with powered contact lenses. Either system may incorporate software implementations of artificial neural networks that learn from input and adjust their output accordingly. Alternately, non-biology based software implementations incorporating statistics, other adaptive algorithms, and/or signal processing may be utilized to create smart systems.

There are a variety of jobs that require the worker to be aware and awake, for example, a truck driver, a security guard and military personnel on duty. It would be counterproductive and lead to potential issues if the worker were to fall asleep while performing their duties. Many of these jobs are such that the worker is required to have mobility while performing their duties and as such a fixed base monitoring system is not practical for providing monitoring of these workers. Furthermore, there are many jobs requiring regulated amounts of sleep in off-hours, which are manually logged by the worker instead of having automatic logging of the worker's sleep to provide better records.

Accordingly, there exists a need for a means and method for detecting certain physiological functions, such as a length of eye closure or a blink, and utilizing them to activate and/or control an electronic or powered ophthalmic lens according to the type of blink sequence detected by a sensor. The sensor being utilized needs to be sized and configured for use in a contact lens. In addition there exists a need to detect the position of a user's eyelids. An eyelid position sensor could be used to detect that a user is falling asleep, for example to trigger an appropriate alert to keep the user awake. There are existing systems for detecting lid position; however they are limited to devices like camera imagers, image recognition, and infrared emitter/detector pairs which rely on reflection off the eye and eyelid. Existing systems to detect lid position also rely on the use of spectacles or clinical environments and are not easily contained within a contact lens.

SUMMARY OF THE INVENTION

The electronic ophthalmic lens with lid position sensor in accordance with the present invention overcomes the limitations associated with the prior art as briefly described above. This lid position sensor may be integrated into a contact lens instead of requiring a clinical environment or spectacles as is common for existing eye-facing detection systems. The lid position sensor is of the appropriate size and current consumption for use in a contact lens. It also outputs the information necessary for determining whether the wearer is asleep or awake.

In accordance with one aspect, the present invention is directed to a powered ophthalmic lens. The powered ophthalmic lens comprises a contact lens, and an eyelid position sensor system incorporated into the contact lens, the eyelid position sensor system including a sensor array having at least one of a plurality of individual sensors spaced vertically from each other and a continuous pressure and/or capacitance sensor to detect eyelid position, a system controller configured to sample each individual sensor in the sensor array to detect eyelid position and provide an output control signal, and at least one alert mechanism configured to receive the output control signal and implement a predetermined function of alerting of the wearer and/or logging data regarding sleep of the wearer. In at least one embodiment, the contact lens includes an optic zone and a peripheral zone in which the electrical components are located. In an alternative embodiment, the eyelid position sensor system includes a strip sensor in place of the plurality of individual sensors.

In accordance with yet another aspect, the present invention is directed to a powered ophthalmic lens. The powered ophthalmic lens comprises an intraocular lens, and an eyelid position sensor system incorporated into the intraocular lens, the eyelid position sensor system including a sensor array having a plurality of individual sensors spaced vertically from each other to detect eyelid position, a system controller configured to sample each individual sensor in the sensor array to detect eyelid position and provide an output control signal, and at least one alert mechanism configured to receive the output control signal and implement a predetermined function of alerting of the wearer and/or logging data regarding sleep of the wearer.

In at least one embodiment, a powered ophthalmic lens includes: a contact lens; and an eyelid position sensor system incorporated into the contact lens, the eyelid position sensor system including a sensor array having a plurality of individual sensors vertically spaced from each other to detect eyelid position, a system controller configured to sample each individual sensor in the sensor array to detect eyelid position and provide an output control signal, and at least one alert mechanism configured to receive the output control signal and capable of at least one of providing an alert and storing data in response to a determination by the system controller that the eyelid has been closed for a period of time indicative of at least one of onset of sleep and drowsiness. Further to this embodiment, the alert mechanism includes at least one of a light source positioned on the lens to provide a light onto at least one of a retina of a wearer of the lens and the lens itself as the alert, a transducer to vibrate an eye of a wearer of the lens as the alert, an electrical simulator configured to stimulate at least one of a corneal surface and at least one sensory nerve of a cornea, and components to provide optic zone modification of an optic zone of the contact lens. Further to the other embodiments of this paragraph, the lens further includes at least one electronic communication component in communication with the alert mechanism and configured to transmit a notification to an external device in response to the alert received from the alert mechanism. Further to the other embodiments of this paragraph, the lens further includes a clock, and the alert mechanism includes associated memory for storing an initiation of sleep in response to the determination of onset of sleep by the system controller and a termination of sleep in response to a determination of a wearer waking up by the system controller, the alert mechanism configured to store a time stamp from the clock with the initiation of sleep and the termination of sleep. Further to the previous embodiment, the lens further includes at least one electronic communication component connected to the memory and the clock, and the at least one electronic communication component configured to retrieve data from the memory and a time stamp from the clock in response to an external inquiry for the stored data. Further to the other embodiments of this paragraph, the system controller operates in one of at least two states based on a state input received by the system controller, where the at least two states include an awake operation state and an asleep operation state and the at least two states control the operation of the at least one alert mechanism as to whether the alert is provided based on the detection of onset of sleep by the system controller. Further to the other embodiments of this paragraph, the plurality of individual sensors include photosensors for detecting light incident on the eye; and the eyelid position sensor system further includes a multiplexer configured to receive multiple inputs from the photosensors and output a single signal, an analog-to-digital converter configured to convert the analog signal from the amplifier to a sampled, digital signal for further signal processing, and a digital signal processor configured to receive an output from the analog-to-digital converter and perform digital signal processing, including one or more of filtering, processing and detecting sampled data to permit incident light detection for downstream use. Further to the prior embodiment, the digital signal processor includes associated memory storing two sets of blink templates and blink masks for use by the digital signal processor based on operational state of the lens as determined in response to wearer instructions. Further to the other embodiments of this paragraph, the lens further includes a power supply. Further to the other embodiments of this paragraph, the plurality of individual sensors include capacitive touch sensors for detecting contact or proximity and outputting a signal indicative thereof; and the sensor system further includes sensor conditioners that output a signal proportional to capacitance for downstream use. Further to the prior embodiment, the eyelid position sensor system further includes a multiplexer configured to receive multiple inputs from the sensor conductors and output a single signal to the system controller. Further to the other embodiment of this paragraph, the eyelid position sensor system further includes a communication channel for coordinating action between pairs of powered contact lenses. Further to the other embodiments of this paragraph, the lens further includes a pupil position system having at least one accelerometer for tracking eye movement, the pupil position system in communication with the system controller such that the system controller samples the at least one accelerometer to detect pupil position; and the system controller uses both pupil position and eyelid position to determine at least one of the onset of sleep and drowsiness.

In at least one embodiment, a powered ophthalmic lens includes: a contact lens; and an eyelid position sensor system incorporated into the contact lens, the eyelid position sensor system including at least one sensor strip having a plurality of vertical points along its length to detect eyelid position, a system controller configured to sample each individual sensor in the sensor array to detect eyelid position and provide an output control signal, and at least one alert mechanism configured to receive the output control signal and capable of at least one of providing an alert and storing data in response to a determination by the system controller that the eyelid has been closed for a period of time indicative of at least one of onset of sleep and drowsiness. Further to the prior embodiment, the alert mechanism includes at least one of the following: a light source positioned on the lens to provide a light onto at least one of a retina of a wearer of the lens and the lens itself as the alert, a transducer to vibrate an eye of a wearer of the lens as the alert, an electrical simulator configured to stimulate at least one of a corneal surface and at least one sensory nerve of a cornea, and a transducer that provides optic zone modification of an optic zone of the contact lens. Further to the other embodiments of this paragraph, the lens further includes a clock, and the alert mechanism includes associated memory for storing an initiation of sleep in response to the determination of onset of sleep by the system controller and a termination of sleep in response to a determination of a wearer waking up by the system controller, the alert mechanism configured to store a time stamp from the clock with the initiation of sleep and the termination of sleep.

In at least one embodiment, a powered ophthalmic lens includes: an intraocular lens; and an eyelid position sensor system incorporated into the intraocular lens, the eyelid position sensor system including a sensor array having a plurality of individual sensors to detect eyelid position, a system controller configured to sample each individual sensor in the sensor array to detect eyelid position to determine at least one of drowsiness and sleep onset of a wearer and provide an output control signal, and at least one alert mechanism configured to receive the output control signal.

In at least one embodiment it will be advantageous to provide a mechanism in which to awaken the worker in response to detection of the worker's eyelids being closed for a period of time indicating the worker is asleep. In a further embodiment, the system includes a mechanism to alert the worker that they are drifting towards sleep based on a detected pattern of eyelid closures different than a typical blink pattern or an indication of blink instructions being provided by worker.

The present invention relates to a powered or electronic ophthalmic lens which may incorporate an eyelid or lid position sensor. It is known that the eyelids protect the globe in a number of ways, including the blink reflex and the tear spreading action. The blink reflex of the eyelids prevents trauma to the globe by rapidly closing upon a perceived threat to the eye. Blinking also spreads tears over the globe's surface to keep it moist and rinse away bacteria and other foreign matter. But the movement of the eyelids may also indicate other actions or functions at play. An eyelid position sensor may be utilized to alert an individual wearing an electronic ophthalmic lens that he or she is in danger of falling asleep.

The present invention more generally relates to a powered contact lens comprising an electronic system, which performs any number of functions, including actuating a variable-focus optic if included. The electronic system includes one or more batteries or other power sources, power management circuitry, one or more sensors, clock generation circuitry, control algorithms and circuitry, and lens driver circuitry.

Control of a powered ophthalmic lens may be accomplished through a manually operated external device that communicates with the lens wirelessly, such as a hand-held remote unit. Alternately, control of the powered ophthalmic lens may be accomplished via feedback or control signals directly from the wearer. For example, sensors built into the lens may detect blinks and/or blink patterns. Based upon the pattern or sequence of blinks, the powered ophthalmic lens may change operation state, for example, between an awake operation state and an asleep operation state. Alternatively, the sensors may include, for example, a pressure sensor, a reed switch, a salinity sensor, a biosensor, and a capacitive sensor to provide a signal indicating the lens has been inserted.

The blink detection algorithm is a component of the system controller which detects characteristics of blinks, for example, if the lid is open or closed, the duration of the blink open or closed, the inter-blink duration, and the number of blinks in a given time period. The algorithm in accordance with the present invention relies on sampling light incident on the eye at a certain sample rate. Pre-determined blink patterns are stored and compared to the recent history of incident light samples. When patterns match, the blink detection algorithm triggers activity in the system controller, for example, to switch to a particular operation state.

The blink detection algorithm and associated circuitry of the present invention preferably operate over a reasonably wide range of lighting conditions and is preferably able to distinguish an intentional blink sequence or closed eyelids from involuntary blinks. It is also preferred that minimal training is required to utilize intentional blinks to activate and/or control the powered ophthalmic lens. The blink detection algorithm and associated circuitry of the present invention provides a safe, low cost, and reliable means and method for detecting blinks via a powered or electronic contact lens, which also has a low rate of power consumption and is scalable for incorporation into an ophthalmic lens, for at least one of activating or controlling a powered or electronic ophthalmic lens.

The present invention is also directed to a powered or electronic ophthalmic lens that incorporates an eyelid or lid position sensor.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
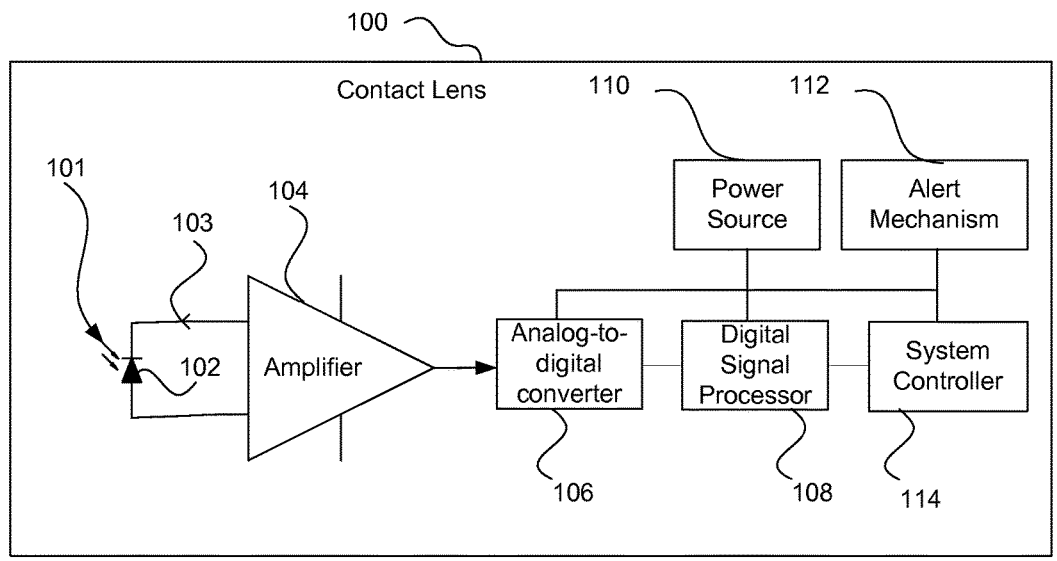
FIG. 1 illustrates a contact lens comprising a blink detection system in accordance with some embodiments of the present invention.

Conventional contact lenses are polymeric structures with specific shapes to correct various vision problems as briefly set forth above. To achieve enhanced functionality, various circuits and components may be integrated into these polymeric structures. For example, control circuits, microprocessors, communication devices, power supplies, sensors, alert mechanisms, light-emitting diodes, and miniature antennas may be integrated into contact lenses via custom-built optoelectronic components to not only correct vision, but to enhance vision as well as provide additional functionality as is explained herein. Electronic and/or powered contact lenses may be designed to provide enhanced vision via zoom-in and zoom-out capabilities, or just simply modifying the refractive capabilities of the lenses. Electronic and/or powered contact lenses may be designed to enhance color and resolution, to display textual information, to translate speech into captions in real time, to offer visual cues from a navigation system, and to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. In addition, sensors built into the lenses may be utilized to detect light incident on the eye to compensate for ambient light conditions or for use in determining blink patterns and whether the wearer is asleep or awake.

The powered or electronic contact lens of the present invention comprises the necessary elements to correct and/or enhance the vision of patients with one or more of the above described vision defects or otherwise perform a useful ophthalmic function. In addition, the electronic contact lens may be utilized simply to enhance normal vision or provide a wide variety of functionality as described above. The electronic contact lens may comprise a variable-focus optic lens, an assembled front optic embedded into a contact lens or just simply embedding electronics without a lens for any suitable functionality. The electronic lens of the present invention may be incorporated into any number of contact lenses as described above. In addition, intraocular lenses may also incorporate the various components and functionality described herein. However, for ease of explanation, the disclosure will focus on an electronic contact lens to correct vision defects intended for single-use daily disposability.

The present invention may be employed in a powered ophthalmic lens or powered contact lens comprising an electronic system, which actuates a variable-focus optic or any other device or devices configured to implement any number of numerous functions that may be performed. The electronic system includes one or more batteries or other power sources, power management circuitry, one or more sensors, clock generation circuitry, control algorithms and circuitry, and lens driver circuitry. The complexity of these components may vary depending on the required or desired functionality of the lens. Alternatively, the contact lens may just monitor drowsiness and/or sleep of the wearer.

Control of an electronic or a powered ophthalmic lens may be accomplished through a manually operated external device that communicates with the lens, such as a hand-held remote unit. For example, a fob may wirelessly communicate with the powered lens based upon manual input from the wearer. Alternately, control of the powered ophthalmic lens may be accomplished via feedback or control signals directly from the wearer. For example, sensors built into the lens may detect blinks, blink patterns, and/or eyelid closures. Based upon the pattern or sequence of blinks, the powered ophthalmic lens may change operation state, for example, the operation state of the lens or its operation state for detecting sleep by the wearer. A further alternative is that the wearer has no control over operation of the powered ophthalmic lens.

A blink detection algorithm is a component of the system controller which detects characteristics of blinks, for example, is the lid open or closed, the duration of the blink, the inter-blink duration, the number of blinks in a given time period, and the length of lid closure. The algorithm in accordance with the present invention relies on sampling light incident on the eye at a certain sample rate. Pre-determined blink patterns are stored and compared to the recent history of incident light samples. When patterns match, the blink detection algorithm may trigger activity in the system controller, for example, to activate the lens driver to change the refractive power of the lens or to change the operation state of the lens. The blink detection algorithm further distinguishes between the pre-determined blink patterns and the eyelid movements associated with drowsiness or sleep onset has occurred.

Blinking is the rapid closing and opening of the eyelids and is an essential function of the eye. Blinking protects the eye from foreign objects, for example, individuals blink when objects unexpectedly appear in proximity to the eye. Blinking provides lubrication over the anterior surface of the eye by spreading tears. Blinking also serves to remove contaminants and/or irritants from the eye. Normally, blinking is done automatically, but external stimuli may contribute as in the case with irritants. However, blinking may also be purposeful, for example, for individuals who are unable to communicate verbally or with gestures can blink once for yes and twice for no. The blink detection algorithm and system of the present invention utilizes blinking patterns that cannot be confused with normal blinking response. In other words, if blinking is to be utilized as a means for controlling an action, then the particular pattern selected for a given action cannot occur at random; otherwise inadvertent actions may occur. As blink speed and/or frequency may be affected by a number of factors, including fatigue, concentration, boredom, eye injury, medication and disease, blinking patterns for control purposes preferably account for these and any other variables that affect blinking. The average length of involuntary blinks is in the range of about one hundred (100) to four hundred (400) milliseconds. Average adult men and women blink at a rate of ten (10) involuntary blinks per minute, and the average time between involuntary blinks is about 0.3 to seventy (70) seconds. Eyelid movements may also indicate other conditions such as drowsiness as the eyelids have a general trend towards closing over a period of time or are closed for a period of time indicating that the wearer is asleep.

An embodiment of the blink detection algorithm may be summarized in the following steps.

1. Define an intentional "blink sequence" that a user will execute for positive blink detection or that is representative of sleep onset.

2. Sample the incoming light level at a rate consistent with detecting the blink sequence and rejecting involuntary blinks.

3. Compare the history of sampled light levels to the expected "blink sequence," as defined by a blink template of values.

4. Optionally implement a blink "mask" sequence to indicate portions of the template to be ignored during comparisons, e.g. near transitions. This may allow for a user to deviate from a desired "blink sequence," such as a plus or minus one (1) error window, wherein one or more of lens activation, control, and focus change can occur. Additionally, this may allow for variation in the user's timing of the blink sequence.

A blink sequence may be defined as follows:
1. blink (closed) for 0.5 s
2. open for 0.5 s
3. blink (closed) for 0.5 s At a one hundred (100) ms sample rate, a twenty (20) sample blink template is given by
  blink_template=[1,1,1, 0,0,0,0,0, 1,1,1,1,1, 0,0,0,0,0, 1,1].

The blink mask is defined to mask out the samples just after a transition (0 to mask out or ignore samples), and is given by
  blink_mask=[1,1,1, 0,1,1,1,1, 0,1,1,1,1, 0,1,1,1,1, 0,1].

Optionally, a wider transition region may be masked out to allow for more timing uncertainty, and is given by
  blink_mask=[1,1,0, 0,1,1,1,0, 0,1,1,1,0, 0,1,1,1,0, 0,1].

Alternate patterns may be implemented, e.g. single long blink, in this case a 1.5 s blink with a 24-sample template, given by
  blink_template=[1,1,1,1,0,0, 0,0,0,0,0,0, 0,0,0,0,0,0, 0,1, 1,1,1,1].

A further alternative pattern may be implemented as indicative of sleep, in this case a 2.4 s blink (or eyes that have closed for sleep) with a 24-sample template, given by
  blink_template=[0,0,0,0,0,0, 0,0,0,0,0,0, 0,0,0,0,0,0, 0,0, 0,0,0,0].

In an alternative embodiment, this blink_template is used without a blink_mask.

It is important to note that the above example is for illustrative purposes and does not represent a specific set of data.

Detection may be implemented by logically comparing the history of samples against the template and mask. The logical operation is to exclusive-OR (XOR) the template and the sample history sequence, on a bitwise basis, and then verify that all unmasked history bits match the template. For example, as illustrated in the blink mask samples above, in each place of the sequence of a blink mask that the value is logic 1, a blink has to match the blink mask template in that place of the sequence. However, in each place of the sequence of a blink mask that the value is logic 0, it is not necessary that a blink matches the blink mask template in that place of the sequence. For example, the following Boolean algorithm equation, as coded in MATLAB®, may be utilized.

matched=not (blink_mask)|not (xor (blink_template, test_sample)), wherein test_sample is the sample history. The matched value is a sequence with the same length as the blink template, sample history and blink_mask. If the matched sequence is all logic 1's, then a good match has occurred. Breaking it down, not (xor (blink_template, test_sample)) gives a logic 0 for each mismatch and a logic 1 for each match. Logic oring with the inverted mask forces each location in the matched sequence to a logic 1 where the mask is a logic 0. Accordingly, the more places in a blink mask template where the value is specified as logic 0, the greater the margin of error in relation to a person's blinks is allowed. MATLAB® is a high level language and implementation for numerical computation, visualization and programming and is a product of MathWorks, Natick, Mass. It is also important to note that the greater the number of logic 0's in the blink mask template, the greater the potential for false positive matched to expected or intended blink patterns. It should be appreciated that a variety of expected or intended blink patterns may be programmed into a device with one or more active at a time and in at least one embodiment control the use of particular blink patterns to be used in a particular operation state. More specifically, multiple expected or intended blink patterns may be utilized for the same purpose or functionality, or to implement different or alternate functionality. For example, one blink pattern may be utilized to cause the lens to change operation state between at least an asleep operation state and an awake operation state. The blink detection in at least one embodiment also can detect when the eyelids remain closed, which would be detected as a continuous blink; the eyelids have a movement trajectory to closing for sleep, which would be detected as a partial blink or series of partial blinks such as when a portion of the sensors are covered by an eyelid after a blink has occurred; and eyelid droop, which would be detected as a change in the steady state position of the upper and/or lower eyelid from its normal steady state position with or without confirmation of gaze position and/or head droop.

An example of a way to determine if the wearer is nodding off is by tracking the length of blink period widths and eyelids open period widths. Alternatively, also partial eyelids open period widths are tracked in addition or instead of eyelids open period widths. Typically the ratio will be 1:15 to 1:22 between blinks and eyelids open, but as the wearer approaches sleep the length of blink period widths will increase while eyelid open period widths will decrease. In a system that includes a plurality of registers for storing the period widths, a running series of ratios between blink periods and eyelid open periods may be maintained such that as that trend of ratios approaches a predetermined drowsy threshold, the wearer is probably starting to doze off. Examples of the predetermined drowsy threshold include, but are not limited to, one to 1, 2, 3, 4, 5, and 10. The system controller would be configured to compare the ratios and track the period lengths over a rolling window. In an alternative embodiment, the system controller would retain only period width information associated with non-standard blinks for a predetermined window as the wearer may notice they are dozing and be more attentive before having another lengthy blink period.

In an alternative embodiment, the system controller would determine a ratio of blink to eyelids open for the wearer at a predetermined time(s). Examples of the predetermined time(s) include, but are not limited to, shortly after lens insertion, one hour increments, two hour increments, four hour increments and any combination of these. In an alternative or further embodiment, the system controller would determine a ratio of blink to eyelids open for the wearer when a change of focus of one or both eyes is detected or there is an increase in the time between blinks such that the increase exceeds a predetermined threshold indicating, for example, that the wearer is concentrating on something or boredom has set in for the wearer. This wearer-specific ratio would be used to calculate the predetermined drowsy threshold. An example of the calculation includes taking a fraction of the wearer-specific ratio, such as reducing by a quarter (e.g., 1:20 to 1:15), half (e.g., 1:20 to 1:10) or three quarters (e.g., 1:20 to 1:5). Based on this example, one of ordinary skill in the art should appreciate that a variety of reductions are possible.

In a further embodiment, the level of eye lid droop is monitored for the wearer such that when the steady state for the eyelid position has decreased from the initial steady state for the wearer, then this will trigger the system controller to have the alert mechanism act. The steady state for the eyelids in at least one embodiment is based on where the eyelids open to after blinking as determined by the eyelid position sensor system. The steady state position in at least one embodiment is stored in a register for comparison purposes. The system controller would have a buffer or other memory to store a running series of eyelid position measurements for comparison to the steady state measurement stored in the register.

A further example of nodding off is the speed at which the eyelids open and close during a blink. A study found that the mean time for eyelid closure was 92 msec plus or minus 17 msec and the mean time for eyelid opening was 242 msec plus or minus 55 msec. BanderWerf, et al., "Eyelid Movements: Behavioral Studies of Blinking in Humans under Different Stimulus Conditions," Journal of Physiology, May 2003, vol. 89, no. 5, pp. 2784-2796. The system controller in at least one embodiment maintains a running list of times for at least one of eyelid closure and eyelid opening to allow for a determination if there is a change in speed of the monitored eyelid movement. Such that when the speed over a series of blinks slows, then the system controller has a basis on which to determine that the wearer is drowsy. In a further embodiment, the speed is measured as a ratio between the distance from the closed eyelid position and the open eyelid position and the time to travel between these two points.

A still further example of nodding off is a decrease in the Saccades movement of the pupil of the lens wearer. It is normal when a person is awake that their eyes dart about in a Saccades movement due to physiological considerations. As a person becomes drowsy, these movements will decrease while the eyelids are open. The eye movement sensor system in at least one embodiment is used to track movement of the pupil and can provide this information to the system controller for comparison along a running list of eye movement data reflecting the volume, the length, and the speed of pupil movement.

In a further embodiment, the system controller would utilize signals from the accelerometer to determine if the wearer's head is beginning to droop in conjunction with any longer blink period width, then the system controller in at least one embodiment will lower the drowsy threshold or alternatively use the drooping head as confirmation that the wearer is beginning to doze off and requires alerting.

FIG. 1 illustrates, in block diagram form, a contact lens 100, comprising an electronic blink detector system, in accordance with an embodiment of the present invention. In this embodiment, the electronic blink detector system may comprise a photosensor 102, an amplifier 104, an analog-to-digital converter (or ADC) 106, a digital signal processor 108, a power source 110, an alert mechanism 112, and a system controller 114.

When the contact lens 100 is placed onto the front surface of a user's eye the electronic circuitry of the blink detector system may be utilized to implement the blink detection algorithm of the present invention. The photosensor 102, as well as the other circuitry, is configured to detect blinks, various blink patterns produced by the user's eye, and/or level of eyelid closure.

In this embodiment, the photosensor 102 may be embedded into the contact lens 100 and receives ambient light 101, converting incident photons into electrons and thereby causing a current, indicated by arrow 103, to flow into the amplifier 104. The photosensor or photodetector 102 may comprise any suitable device. In one embodiment, the photosensor 102 comprises a photodiode. In at least one embodiment, the photodiode is implemented in a complimentary metal-oxide semiconductor (CMOS process technology) to increase integration ability and reduce the overall size of the photosensor 102 and the other circuitry. The current 103 is proportional to the incident light level and decreases substantially when the photodetector 102 is covered by an eyelid. The amplifier 104 creates an output proportional to the input, with gain, and may function as a transimpedance amplifier which converts input current into output voltage. The amplifier 104 may amplify a signal to a usable level for the remainder of the system, such as giving the signal enough voltage and power to be acquired by the ADC 106. For example, the amplifier may be necessary to drive subsequent blocks since the output of the photosensor 102 may be quite small and may be used in low-light environments. The amplifier 104 may be implemented as a variable-gain amplifier, the gain of which may be adjusted by the system controller 114, in a feedback arrangement, to maximize the dynamic range of the system. In addition to providing gain, the amplifier 104 may include other analog signal conditioning circuitry, such as filtering and other circuitry appropriate to the photosensor 102 and amplifier 104 outputs. The amplifier 104 may comprise any suitable device for amplifying and conditioning the signal output by the photosensor 102. For example, the amplifier 104 may simply comprise a single operational amplifier or a more complicated circuit comprising one or more operational amplifiers. As set forth above, the photosensor 102 and the amplifier 104 are configured to detect and isolate blink sequences based upon the incident light intensity received through the eye and convert the input current into a digital signal usable ultimately by the system controller 114. The system controller 114 is preferably preprogrammed or pre-configured to recognize various blink sequences, blink patterns, an/or eyelid closures (partial or complete) in various light intensity level conditions and provide an appropriate output signal to the alert mechanism 112. The system controller 114 also comprises associated memory.

In this embodiment, the ADC 106 may be used to convert a continuous, analog signal output from the amplifier 104 into a sampled, digital signal appropriate for further signal processing. For example, the ADC 106 may convert an analog signal output from the amplifier 104 into a digital signal that may be usable by subsequent or downstream circuits, such as a digital signal processing system or microprocessor 108. A digital signal processing system or digital signal processor 108 may be utilized for digital signal processing, including one or more of filtering, processing, detecting, and otherwise manipulating/processing sampled data to permit incident light detection for downstream use. The digital signal processor 108 may be preprogrammed with the blink sequences and/or blink patterns described above along with blink sequence indicating prolonged eyelid closure or eyelid drift. The digital signal processor 108 also comprises associated memory, which in at least one embodiment includes template and masks sets to detect, for example, blink patterns for each operation state as selected by the system controller 114. The digital signal processor 108 may be implemented utilizing analog circuitry, digital circuitry, software, or a combination thereof. In the illustrated embodiment, it is implemented in digital circuitry. The ADC 106 along with the associated amplifier 104 and digital signal processor 108 are activated at a suitable rate in agreement with the sampling rate previously described, for example every one hundred (100) ms.

A power source 110 supplies power for numerous components comprising the blink detection system. The power may be supplied from a battery, energy harvester, or other suitable means as is known to one of ordinary skill in the art. Essentially, any type of power source 110 may be utilized to provide reliable power for all other components of the system. A blink sequence in at least one embodiment may be utilized to change the operation state of the system and/or the system controller. Furthermore, the system controller 114 may control other aspects of a powered contact lens depending on input from the digital signal processor 108, for example, changing the focus or refractive power of an electronically controlled lens through an actuator.

In at least one embodiment, the system controller 114 will determine the operation state of the lens based on a received blink pattern to set the operation state as an asleep operation state or an awake operation state although in an alternative embodiment other states are possible. Further to this embodiment, the operation state will determine a set of blink templates and masks to be used by the digital signal processor 108 in that operation state along with control what the alert mechanism 112 does in response to the system controller 114 detecting the wearer has fallen asleep. In an alternative embodiment, the lens will be intended for use during a work shift and as such will operate in accordance with the described awake operation state leading to one set of blink templates and masks being used by the digital signal processor 108 for a particular wearer. In a further alternative embodiment, the lens intended for use during a work shift will operate using just a blink template indicating sleep onset and not change operational state based on any blink pattern by the wearer.

Figure 2:
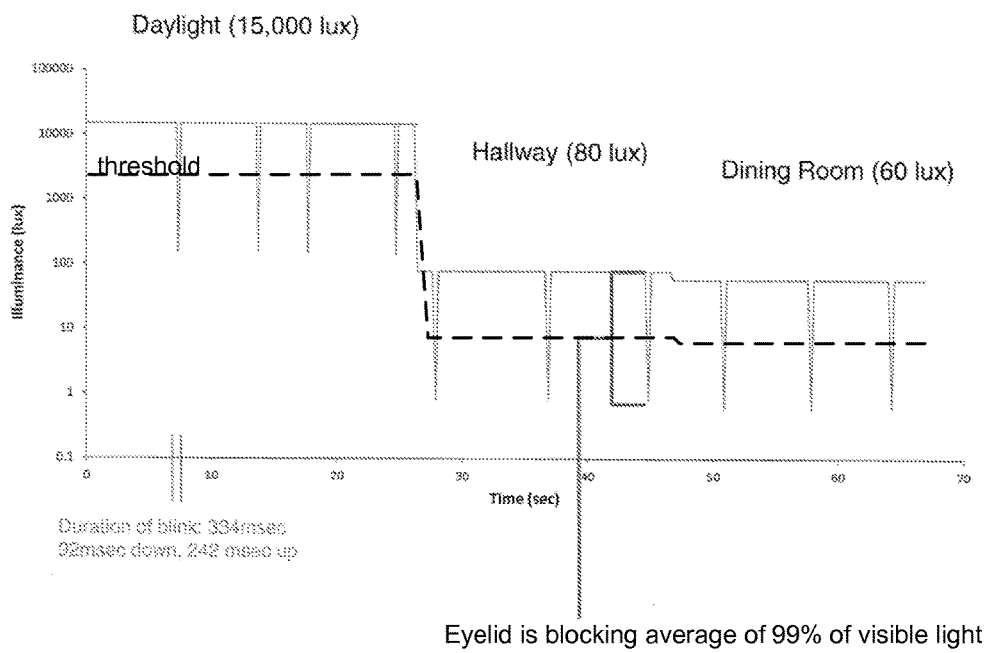
FIG. 2 illustrates a graphical representation of light incident on the surface of the eye versus time, illustrating a possible involuntary blink pattern recorded at various light intensity levels versus time and a usable threshold level based on some point between the maximum and minimum light intensity levels in accordance with the present invention.

The system controller 114 uses the signal from the photosensor chain; namely, the photosensor 102, the amplifier 104, the ADC 106 and the digital signal processing system 108, to compare sampled light levels to blink activation patterns. Referring to FIG. 2, a graphical representation of blink pattern samples recorded at various light intensity levels versus time and a usable threshold level is illustrated. Accordingly, accounting for various factors may mitigate and/or prevent error in detecting blinks when sampling light incident on the eye, such as accounting for changes in light intensity levels in different places and/or while performing various activities. Additionally, when sampling light incident on the eye, accounting for the effects that changes in ambient light intensity may have on the eye and eyelid may also mitigate and/or prevent error in detecting blinks, such as how much visible light an eyelid blocks when it is closed in low-intensity light levels and in high-intensity light levels. In other words, in order to prevent erroneous blinking patterns from being utilized to control, the level of ambient light is preferably accounted for as is explained in greater detail below.

For example, in a study, it has been found that the eyelid on average blocks approximately ninety-nine (99) percent of visible light, but at lower wavelengths less light tends to be transmitted through the eyelid, blocking out approximately 99.6 percent of visible light. At longer wavelengths, toward the infrared portion of the spectrum, the eyelid may block only thirty (30) percent of the incident light. What is important to note; however, is that light at different frequencies, wavelengths and intensities may be transmitted through the eyelids with different efficiencies. For example, when looking at a bright light source, an individual may see red light with his or her eyelids closed. There may also be variations in how much visible light an eyelid blocks based upon an individual, such as an individual's skin pigmentation. As is illustrated in FIG. 2, data samples of blink patterns across various lighting levels are simulated over the course of a seventy (70) second time interval wherein the visible light intensity levels transmitted through the eye are recorded during the course of the simulation, and a usable threshold value is illustrated. The threshold is set at a value in between the peak-to-peak value of the visible light intensity recorded for the sample blink patterns over the course of the simulation at varying light intensity levels. Having the ability to preprogram blink patterns while tracking an average light level over time and adjusting a threshold may be critical to being able to detect when an individual is blinking, as opposed to when an individual is not blinking and/or there is just a change in light intensity level in a certain area.

Referring now again to FIG. 1, in further alternate embodiments, the system controller 114 may receive input from sources including one or more of a blink detector, pressure sensors, an accelerometer(s), photosensors, and a fob control. By way of generalization and based on this disclosure, one skilled in the art should appreciate that the method of determining sleep by the system controller 114 may use of one or more inputs. For example, an electronic or powered contact lens may be programmable specific to an individual user, such as programming a lens to recognize both of an individual's blink patterns and an individual's head movements as detected with an accelerometer during the course of the day, for example, head bobbing while the eyelids are closed. In some embodiments, using more than one input to determine sleep by an electronic contact lens, such as blink detection and head movement, may give the ability for each method to be crosschecked with another before sleep onset is determined to have occurred as will be discussed later in connection with FIGS. 18 and 19. An advantage of crosschecking may include mitigation of false positives, such as minimizing the chance of unintentionally triggering a lens to alert and/or record errant data. In one embodiment, the crosschecking may involve a voting scheme, wherein a certain number of conditions are met prior to a sleep determination. In a further embodiment, the crosschecking may involve a weighted average, wherein certain inputs will be deemed more important than other inputs such as lid closure and head orientation.

The alert mechanism 112 may comprise any suitable device for implementing a specific alert to the wearer based upon a received command signal. For example, if a sleep pattern is matched compared to a sampled light level as described above, the system controller 114 may enable the alert mechanism 112, such as a light (or light array) to pulse a light or cause a physical wave to pulsate into the wearer's retina (or alternatively across the lens) or to log data regarding the onset of sleep. Further examples of the alert mechanism 112 include an electrical device; a mechanical device including, for example, piezoelectric devices, transducers, vibrational devices, chemical release devices with examples including the release of chemicals to cause an itching, irritation or burning sensation, and acoustic devices; a transducer providing optic zone modification of an optic zone of the contact lens such as modifying the focus and/or percentage of light transmission through the lens; a magnetic device; an electromagnetic device; a thermal device; an optical coloration mechanism with or without liquid crystal, prisms, fiber optics, and/or light tubes to, for example, provide an optic modification and/or direct light towards the retina; an electrical device such as an electrical stimulator to provide a mild retinal stimulation or to stimulate at least one of a corneal surface and one or more sensory nerves of the cornea; or any combination thereof. The alert mechanism 112 receives a signal from the system controller 114 in addition to power from the power source 110 and produces some action based on the signal from the system controller 114. For example, if the system controller 114 signal is indicative of the wearer falling asleep during the awake operation state, then the alert mechanism 112 may alert the wearer that he/she has fallen asleep. In an alternate embodiment, the system controller 114 may output a signal indicating that the wearer has fallen asleep during the asleep operation state, then the alert mechanism 112 will record the information in memory for later retrieval. In an alternative embodiment, the system controller 114 stores the data in the memory associated with the system controller 114 and does not use the alert mechanism 112 for data storage. As discussed later, in at least one embodiment there is a clock that provides a time stamp. As set forth above, the powered lens of the present invention may provide various functionality; accordingly, one or more alert mechanisms may be variously configured to implement the functionality.

Figure 3:
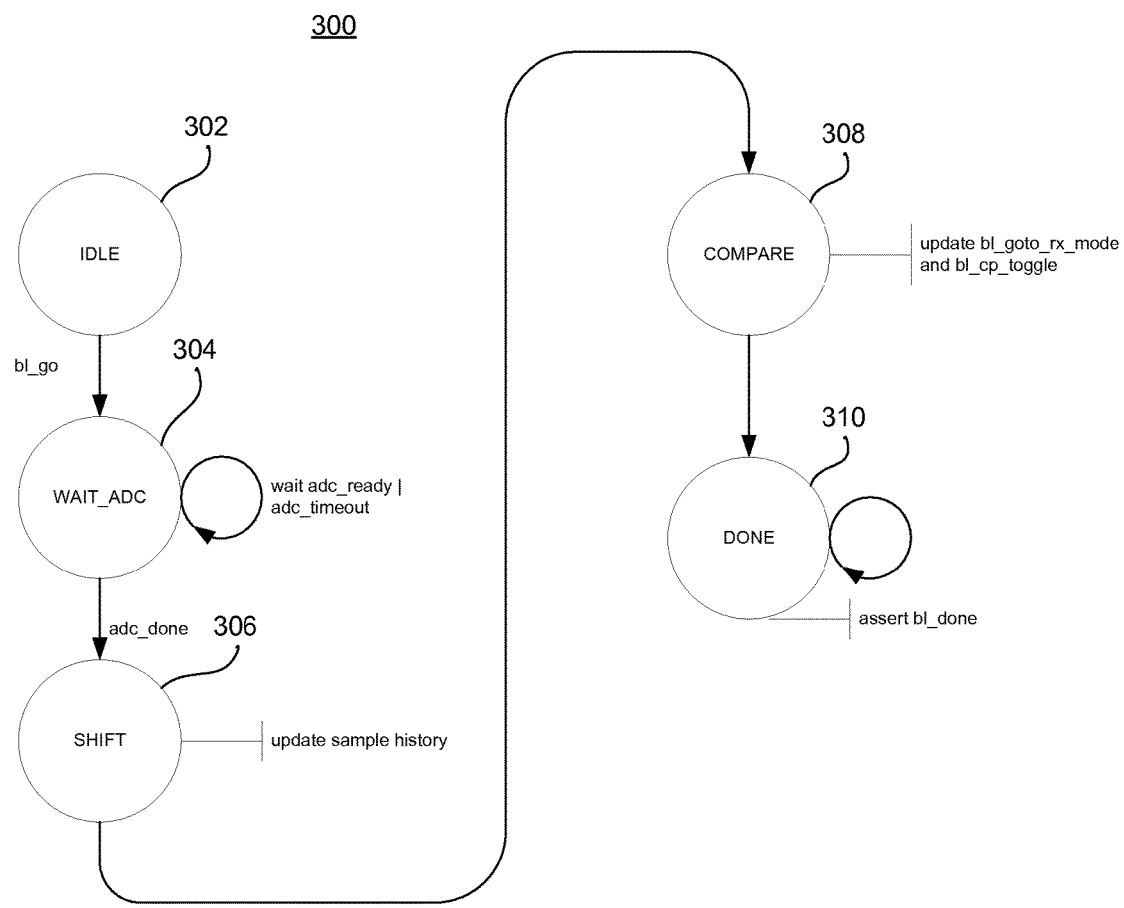
FIG. 3 is a state transition diagram of a blink detection system in accordance with the present invention.

FIG. 3 illustrates a state transition diagram 300 for a blink detection system in accordance with the blink detection algorithm of the present invention. The system starts in an IDLE state 302 waiting for an enable signal bl_go to be asserted. When the enable bl_go signal is asserted, for example, by an oscillator and control circuit which pulses bl_go at a one hundred (100) ms rate commensurate with the blink sampling rate, the state machine then transitions to a WAIT_ADC state 304 in which an ADC is enabled to convert a received light level to a digital value. The ADC asserts an adc_done signal to indicate its operations are complete, and the system or state machine transitions to a SHIFT state 306. In the SHIFT state 306 the system pushes the most recently received ADC output value onto a shift register to hold the history of blink samples. In some embodiments, the ADC output value is first compared to a threshold value to provide a single bit (1 or 0) for the sample value, in order to minimize storage requirements. The system or state machine then transitions to a COMPARE state 308 in which the values in the sample history shift register are compared to one or more blink sequence templates and masks as described above. If a match is detected, one or more output signals may be asserted, such as one to switch the state of the lens to an asleep operation state or an awake operation state or to signal onset of sleep by the wearer. The system or state machine then transitions to the DONE state 310 and asserts a bl_done signal to indicate its operations are complete.

Figure 4:
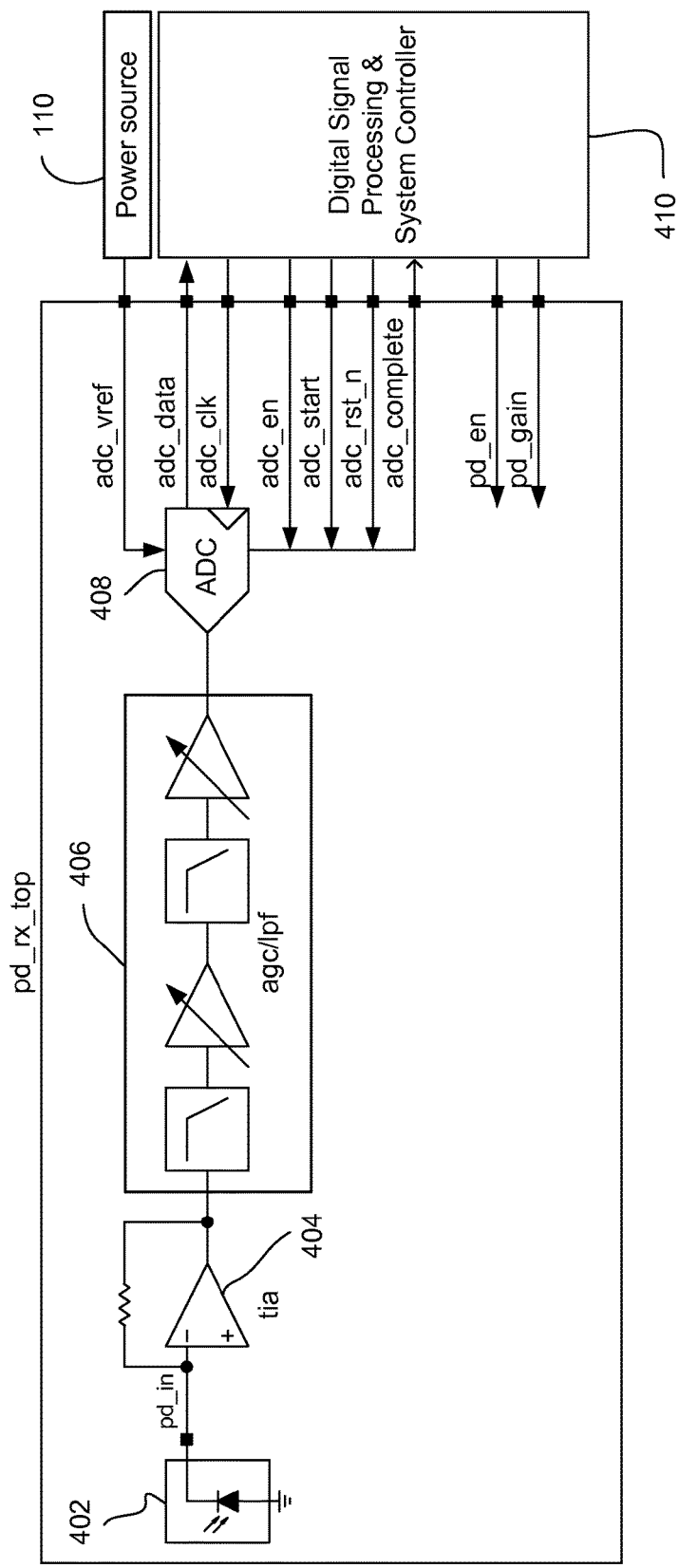
FIG. 4 illustrates a diagrammatic representation of a photodetection path utilized to detect and sample received light signals in accordance with the present invention.

FIG. 4 illustrates a photosensor or photodetector signal path pd_rx_top that may be used to detect and sample received light levels. The signal path pd_rx_top may comprise a photodiode 402, a transimpedance amplifier 404, an automatic gain and low pass filtering stage 406 (AGC/LPF), and an ADC 408. The adc_vref signal is input to the ADC 408 from the power source 110 (see FIG. 1) or alternately it may be provided from a dedicated circuit inside the analog-to-digital converter 408. The output from the ADC 408, adc_data, is transmitted to the digital signal processing and system controller block 108/114 (see FIG. 1). Although illustrated in FIG. 1 as individual blocks 108 and 114, for ease of explanation, the digital signal processing and system controller are preferably implemented on a single block 410. The enable signal, adc_en, the start signal, adc_start, and the reset signal, adc_rst_n are received from the digital signal processing and system controller 410 while the complete signal, adc_complete, is transmitted thereto. The clock signal, adc_clk, may be received from a clock source external to the signal path, pd_rx_top, or from the digital signal processing and system controller 410. It is important to note that the adc_clk signal and the system clock may be running at different frequencies. It is also important to note that any number of different ADCs may be utilized in accordance with the present invention which may have different interface and control signals but which perform a similar function of providing a sampled, digital representation of the output of the analog portion of the photosensor signal path. The photodetect enable, pd_en, and the photodetect gain, pd_gain, are received from the digital signal processing and system controller 410.

Figure 5:
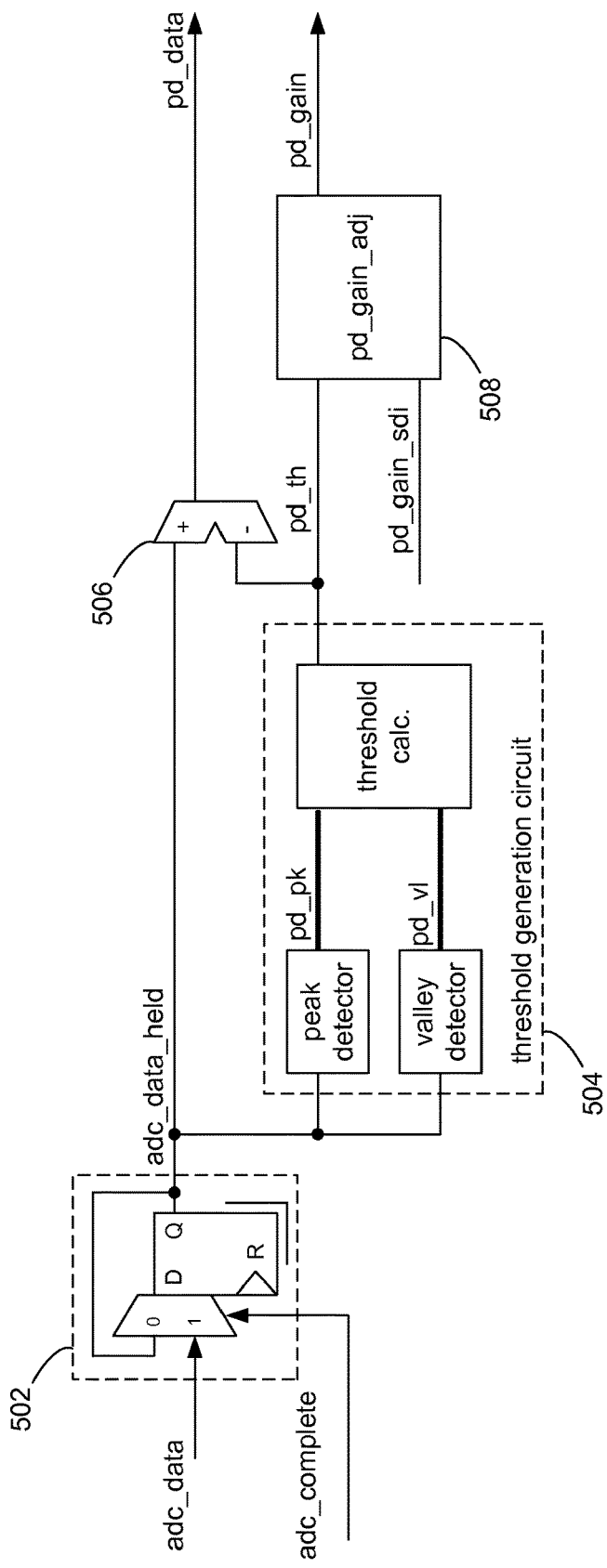
FIG. 5 illustrates a block diagram of digital conditioning logic in accordance with the present invention.

FIG. 5 illustrates a block diagram of digital conditioning logic 500 that may be used to reduce the received ADC signal value, adc_data, to a single bit value pd_data. The digital conditioning logic 500 may comprise a digital register 502 to receive the data, adc_data, from the photodetection signal path pd_rx_top to provide a held value on the signal adc_data_held. The digital register 502 is configured to accept a new value on the adc_data signal when the adc_complete signal is asserted and to otherwise hold the last accepted value when the adc_complete signal is received. In this manner the system may disable the photodetection signal path once the data is latched to reduce system current consumption. The held data value may then be averaged, for example, by an integrate-and-dump average or other averaging methods implemented in digital logic, in the threshold generation circuit 504 to produce one or more thresholds on the signal pd_th. The held data value may then be compared, via comparator 506, to the one or more thresholds to produce a one-bit data value on the signal pd_data. It will be appreciated that the comparison operation may employ hysteresis or comparison to one or more thresholds to minimize noise on the output signal pd_data. The digital conditioning logic may further comprise a gain adjustment block pd_gain_adj 508 to set the gain of the automatic gain and low-pass filtering stage 406 in the photodetection signal path via the signal pd_gain, illustrated in FIG. 4, according to the calculated threshold values and/or according to the held data value. It is important to note that in this embodiment six bit words provide sufficient resolution over the dynamic range for blink detection while minimizing complexity. FIG. 5 illustrates an alternative embodiment that includes providing a pd_gain_sdi control signal from, for example, the serial data interface that allows one to override the automatic gain control determined by gain adjustment block pd_gain_adj 508.

In one embodiment, the threshold generation circuit 504 comprises a peak detector, a valley detector and a threshold calculation circuit. In this embodiment, the threshold and gain control values may be generated as follows. The peak detector and the valley detector are configured to receive the held value on signal adc_data_held. The peak detector is further configured to provide an output value, pd_pk, which quickly tracks increases in the adc_data_held value and slowly decays if the adc_data_held value decreases. The operation is analogous to that of a classic diode envelope detector, as is well-known in the electrical arts. The valley detector is further configured to provide an output value pd_vl which quickly tracks decreases in the adc_data_held value and slowly decays to a higher value if the adc_data_held value increases. The operation of the valley detector is also analogous to a diode envelope detector, with the discharge resistor tied to a positive power supply voltage. The threshold calculation circuit is configured to receive the pd_pl and pd_vl values and is further configured to calculate a mid-point threshold value pd_th_mid based on an average of the pd_pk and pd_vl values. The threshold generation circuit 504 provides the threshold value pd_th based on the mid-point threshold value pd_th_mid.

The threshold generation circuit 504 may be further adapted to update the values of the pd_pk and pd_vl levels in response to changes in the pd_gain value. If the pd_gain value increases by one step, then the pd_pk and pd_vl values are increased by a factor equal to the expected gain increase in the photodetection signal path. If the pd_gain value decreases by one step, then the pd_pk and pd_val values are decreased by a factor equal to the expected gain decrease in the photodetection signal path. In this manner the states of the peak detector and valley detectors, as held in the pd_pk and pd_vl values, respectively, and the threshold value pd_th as calculated from the pd_pk and pd_vl values are updated to match the changes in signal path gain, thereby avoiding discontinuities or other changes in state or value resulting only from the intentional change in the photodetection signal path gain.

In a further embodiment of the threshold generation circuit 504, the threshold calculation circuit may be further configured to calculate a threshold value pd_th_pk based on a proportion or percentage of the pd_pk value. In a preferred embodiment the pd_th_pk may be advantageously configured to be seven eighths of the pd_pk value, a calculation which may be implemented with a simple right shift by three bits and a subtraction as is well-known in the relevant art. The threshold calculation circuit may select the threshold value pd_th to be the lesser of pd_th_mid and pd_th_pk. In this manner, the pd_th value will never be equal to the pd_pk value, even after long periods of constant light incident on the photodiode which may result in the pd_pk and pd_vl values being equal. It will be appreciated that the pd_th_pk value ensures detection of a blink after long intervals. The behavior of the threshold generation circuit is further illustrated in FIG. 9, as discussed subsequently.

Figure 6:
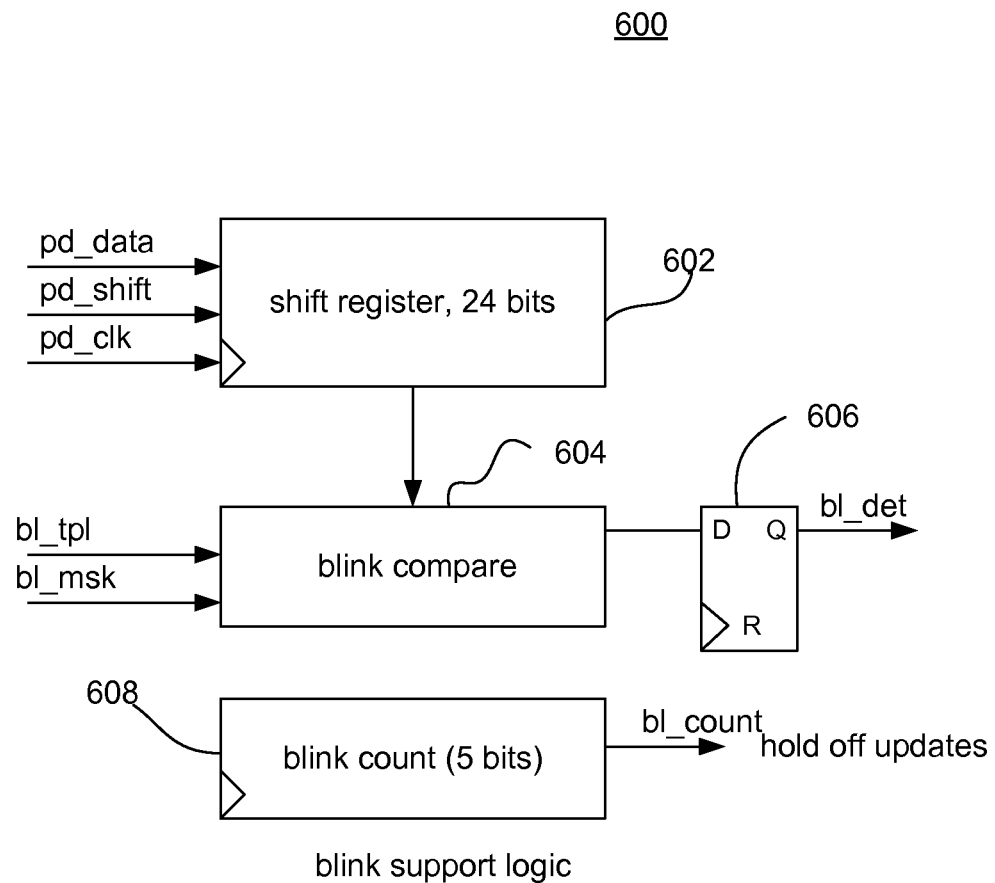
FIG. 6 illustrates a block diagram of digital detection logic in accordance with the present invention.

FIG. 6 illustrates a block diagram of digital detection logic 600 that may be used to implement a digital blink detection algorithm in accordance with an embodiment of the present invention. The digital detection logic 600 may comprise a shift register 602 adapted to receive the data from the photodetection signal path pd_rx_top, FIG. 4, or from the digital conditioning logic, FIG. 5, as illustrated here on the signal pd_data, which has a one bit value. The shift register 602 holds a history of the received sample values, here in a 24-bit register. The digital detection logic 600 further comprises a comparison block 604, adapted to receive the sample history and one or more blink templates bl_tpl and blink masks bl_mask based on operation state (if necessary), and is configured to indicate a match to the one or more templates and masks on one or more output signals that may be held for later use. In at least one embodiment, the operation state determines the set of templates bl_tpl and blink masks _bl_mask to be used by the comparison block 604. In at least one set of the templates bl_tpl, there is at least one sleep template representative of the wearer falling asleep. In an alternative embodiment, the digital detection logic 600 comprises a comparison block, adapted to contain one or more sleep templates, and is configured to indicate a match to the one or more templates and masks on one or more output signals that may be held for later use. In such an alternative embodiment, the lens does not have asleep and awake operation states.

The output of the comparison block 604 is latched via a D flip-flop 606. The digital detection logic 600 may further comprise a counter 608 or other logic to suppress successive comparisons that may be on the same sample history set at small shifts due to the masking operations. In a preferred embodiment the sample history is cleared or reset after a positive match is found, thus requiring a full, new matching blink sequence to be sampled before being able to identify a subsequent match. The digital detection logic 600 may still further comprise a state machine or similar control circuitry to provide the control signals to the photodetection signal path and the ADC. In some embodiments the control signals may be generated by a control state machine that is separate from the digital detection logic 600. This control state machine may be part of the digital signal processing and system controller 410.

Figure 7:
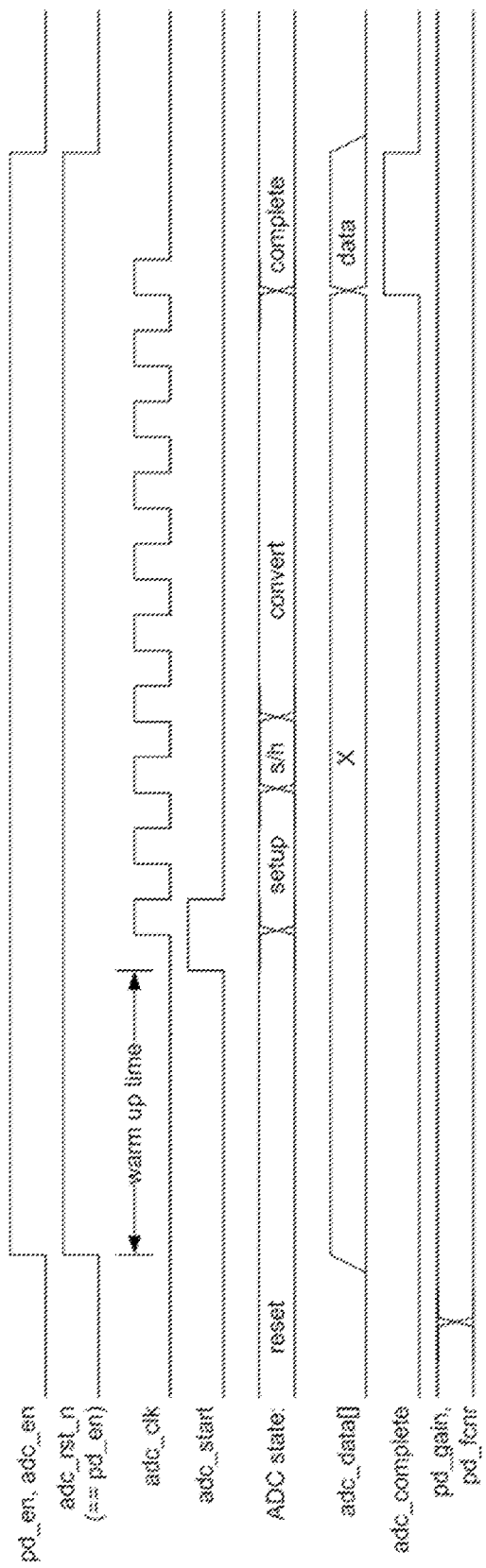
FIG. 7 illustrates a timing diagram in accordance with the present invention.

FIG. 7 illustrates a timing diagram of the control signals provided from a blink detection subsystem to an ADC 408 (FIG. 4) used in a photodetection signal path. The enable and clock signals adc_en, adc_rst_n and adc_clk are activated at the start of a sample sequence and continue until the analog-to-digital conversion process is complete. In one embodiment the ADC conversion process is started when a pulse is provided on the adc_start signal. The ADC output value is held in an adc_data signal and completion of the process is indicated by the analog-to-digital converter logic on an adc_complete signal. Also illustrated in FIG. 7 is the pd_gain signal which is utilized to set the gain of the amplifiers before the ADC. This signal is shown as being set before the warm-up time to allow the analog circuit bias and signal levels to stabilize prior to conversion.

Figure 8A:
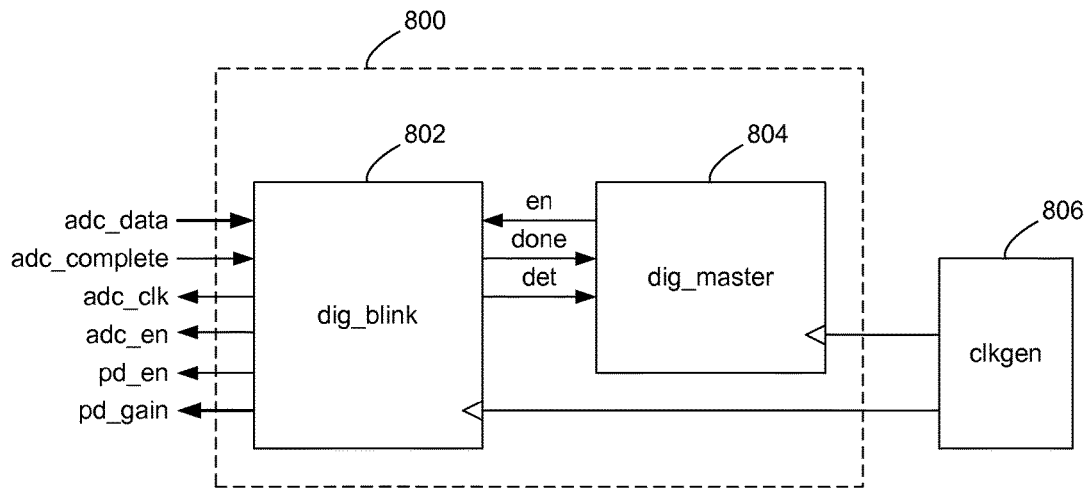
FIGS. 8A and 8B illustrate diagrammatic representations of digital system controllers in accordance with the present invention.

FIG. 8A illustrates a digital system controller 800 comprising a digital blink detection subsystem dig_blink 802. The digital blink detection subsystem dig_blink 802 may be controlled by a master state machine dig_master 804 and may be adapted to receive clock signals from a clock generator clkgen 806 external to the digital system controller 800. The digital blink detection subsystem dig_blink 802 may be adapted to provide control signals to and receive signals from a photodetection subsystem as described above.

The digital blink detection subsystem dig_blink 802 may comprise digital conditioning logic and digital detection logic as described above, in addition to a state machine to control the sequence of operations in a blink detection algorithm. The digital blink detection subsystem dig_blink 802 may be adapted to receive an enable signal from the master state machine 804 and to provide a completion or done indication and a blink detection indication back to the master state machine 804.

Figure 8B:
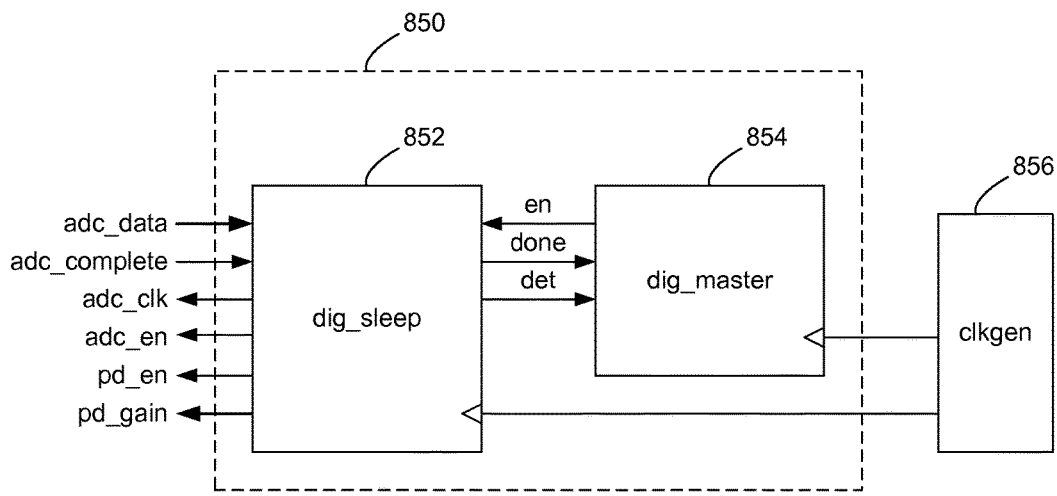

In an alternative embodiment, FIG. 8B illustrates a digital system controller 850 comprising a digital sleep detection subsystem dig_sleep 852. The digital sleep detection subsystem dig_sleep 852 may be controlled by a master state machine dig_master 854 and may be adapted to receive clock signals from a clock generator clkgen 856 external to the digital system controller 850. The digital sleep detection subsystem dig_sleep 852 may be adapted to provide control signals to and receive signals from a photodetection subsystem as described above. The digital sleep detection subsystem dig_sleep 852 may comprise digital conditioning logic and digital detection logic as described above, in addition to a state machine to control the sequence of operations in a sleep detection algorithm. The digital sleep detection subsystem dig_sleep 852 may be adapted to receive an enable signal from the master state machine 854 and to provide a completion or done indication and a sleep detection indication back to the master state machine 854.

In an alternative embodiment to either of the embodiments illustrated in FIGS. 8A and 8B, a time clock is connected to the clock generator 806 to track time since the lens began operation and provide a time stamp signal to the alert mechanism in an embodiment where the alert mechanism records data regarding the initiation and termination of sleep by the wearer such that when data is transmitted (or sent) from the lens to an external device using, for example, at least one electronic communication component, the external device is able to determine what time periods the wearer was asleep while wearing the lens by reverse calculating the time of day based on the time stamp from the lens and the current time on the external device when the data is transmitted as compared to the logged time stamps.

Figure 9A:
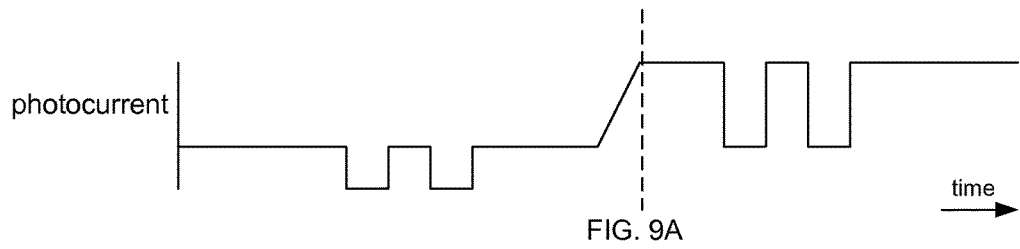
FIGS. 9A through 9G illustrate timing diagrams for automatic gain control in accordance with the present invention.
Figure 9B:
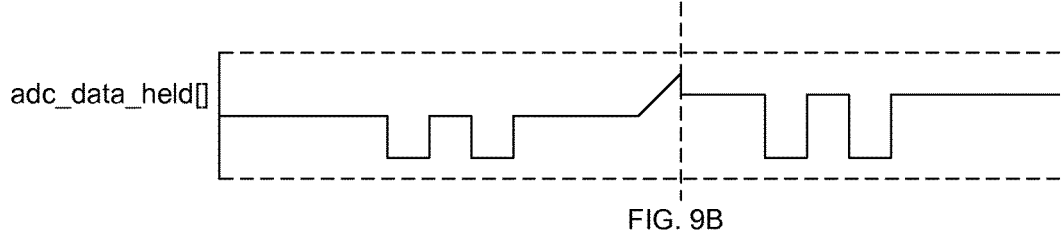
Figure 9C:
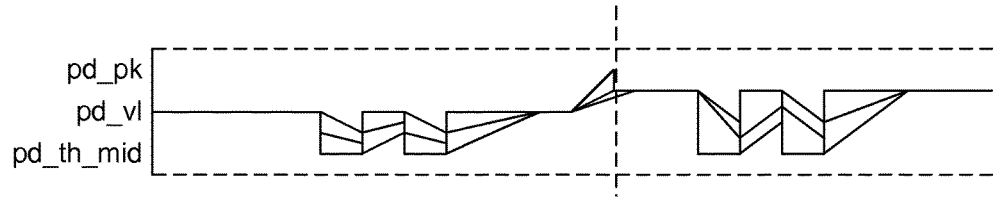
Figure 9D:
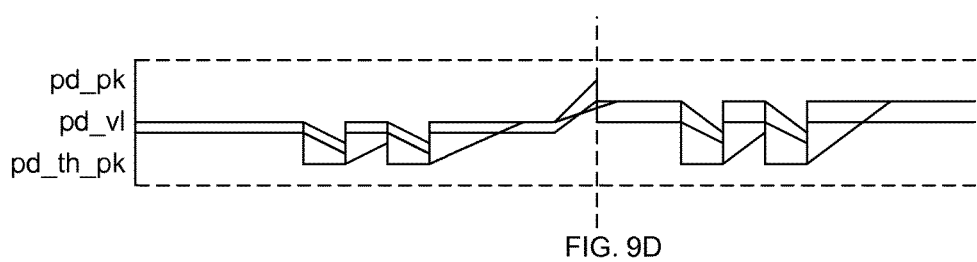
Figure 9E:
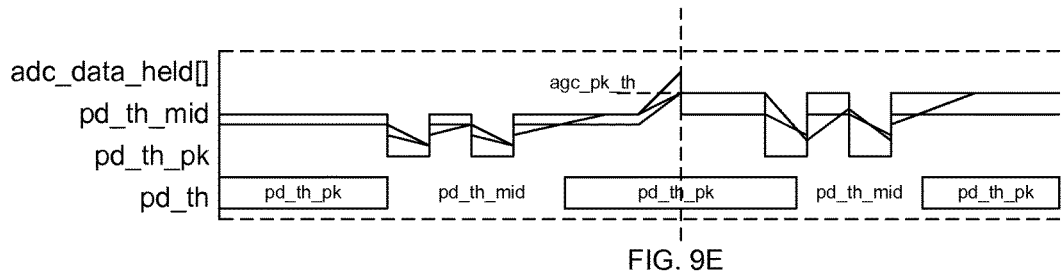
Figure 9F:
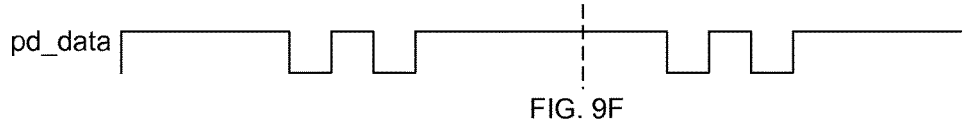
Figure 9G:
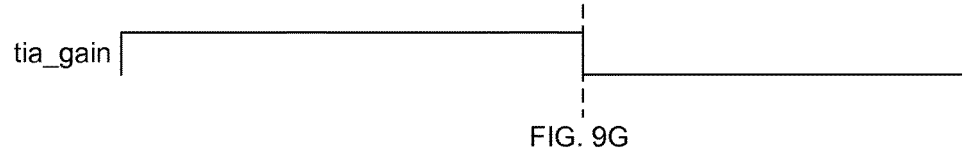

FIGS. 9A-9G provide waveforms to illustrate the operation of the threshold generation circuit and automatic gain control (FIG. 5). FIG. 9A illustrates an example of photocurrent versus time as might be provided by a photodiode in response to varying light levels. In the first portion of the plot, the light level and resulting photocurrent are relatively low compared to in the second portion of the plot. In both the first and second portions of the plot a double blink is seen to reduce the light and photocurrent. Note that the attenuation of light by the eyelid may not be one hundred (100) percent, but a lower value depending on the transmission properties of the eyelid for the wavelengths of light incident on the eye. FIG. 9B illustrates the adc_data_held value that is captured in response to the photocurrent waveform of FIG. 9A. For simplicity, the adc_data_held value is illustrated as a continuous analog signal rather than a series of discrete digital samples. It will be appreciated that the digital sample values will correspond to the level illustrated in FIG. 9B at the corresponding sample times. The dashed lines at the top and bottom of the plot indicate the maximum and minimum values of the adc_data and adc_data_held signals. The range of values between the minimum and maximum is also known as the dynamic range of the adc_data signal. As discussed below, the photodection signal path gain is different (lower) in the second portion of the plot. In general the adc_data_held value is directly proportional to the photocurrent, and the gain changes only affect the ration or the constant of proportionality. FIG. 9O illustrates the pd_pk, pd_vl and pd_th_mid values calculated in response to the adc_data_held value by the threshold generation circuit. FIG. 9D illustrates the pd_pk, pd_vl and pd_th_pk values calculated in response to the adc_data_held value in some embodiments of the threshold generation circuit. Note that the pd_th_pk value is always some proportion of the pd_pk value. FIG. 9E illustrates the adc_data_held value with the pd_th_mid and pd_th_pk values. Note that during long periods of time where the adc_data_held value is relatively constant the pd_th_mid value becomes equal to the adc_data_held value as the pd_vl value decays to the same level. The pd_th_pk value always remains some amount below the adc_data_held value. Also illustrated in FIG. 9E is the selection of pd_th where the pd_th value is selected to be the lower of pd_th_pk and pd_th_mid. In this way the threshold is always set some distance away from the pd_pk value, avoiding false transitions on pd_data due to noise on the photocurrent and adc_data held signals. FIG. 9F illustrates the pd_data value generated by comparison of the adc_data_held value to the pd_th value. Note that the pd_data signal is a two-valued signal which is low when a blink is occurring. FIG. 9G illustrates a value of tia_gain versus time for these example waveforms. The value of tia_gain is set lower when the pd_th starts to exceed a high threshold shown as agc_pk_th in FIG. 9E. It will be appreciated that similar behavior occurs for raising tia_gain when pd_th starts to fall below a low threshold. Looking again at the second portion of each of the FIGS. 9A through 9E the effect of the lower tia_gain is clear. In particular note that the adc_data_held value is maintained near the middle of the dynamic range of the adc_data and adc_data_held signals. Further, it is important to note that the pd_pk and pd_vl values are updated in accordance with the gain change as described above such that discontinuities are avoided in the peak and valley detector states and values due solely to changes in the photodetection signal path gain.

Figure 10:
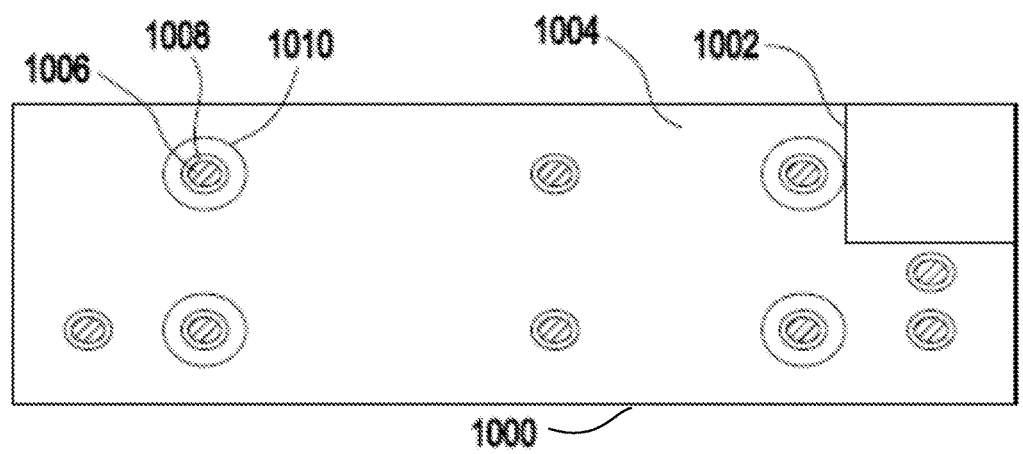
FIG. 10 illustrates a diagrammatic representation of light-blocking and light-passing regions on an integrated circuit die in accordance with the present invention.

FIG. 10 illustrates light-blocking and light-passing features on an integrated circuit die 1000. The integrated circuit die 1000 comprises a light passing region 1002, a light blocking region 1004, bond pads 1006, passivation openings 1008, and light blocking layer openings 1010. The light-passing region 1002 is located above the photosensors (not illustrated), for example an array of photodiodes implemented in the semiconductor process. In at least one embodiment, the light-passing region 1002 permits as much light as possible to reach the photosensors thereby maximizing sensitivity. This may be done through removing polysilicon, metal, oxide, nitride, polyimide, and other layers above the photoreceptors, as permitted in the semiconductor process utilized for fabrication or in post-processing. The light-passing area 1002 may also receive other special processing to optimize light detection, for example an anti-reflective coating, filter, and/or diffuser. The light-blocking region 1004 may cover other circuitry on the die which does not require light exposure. The performance of the other circuitry may be degraded by photocurrents, for example shifting bias voltages and oscillator frequencies in the ultra-low current circuits required for incorporation into contact lenses, as mentioned previously. The light-blocking region 1004 is preferentially formed with a thin, opaque, reflective material, for example aluminum or copper already used in semiconductor wafer processing and post-processing. If implemented with metal, the material forming the light-blocking region 1004 must be insulated from the circuits underneath and the bond pads 1006 to prevent short-circuit conditions. Such insulation may be provided by the passivation already present on the die as part of normal wafer passivation, e.g. oxide, nitride, and/or polyimide, or with other dielectric added during post-processing. Masking permits light blocking layer openings 1010 so that conductive light-blocking metal does not overlap bond pads on the die. The light-blocking region 1004 is covered with additional dielectric or passivation to protect the die and avoid short-circuits during die attachment. This final passivation has passivation openings 1008 to permit connection to the bond pads 1006.

Figure 11:
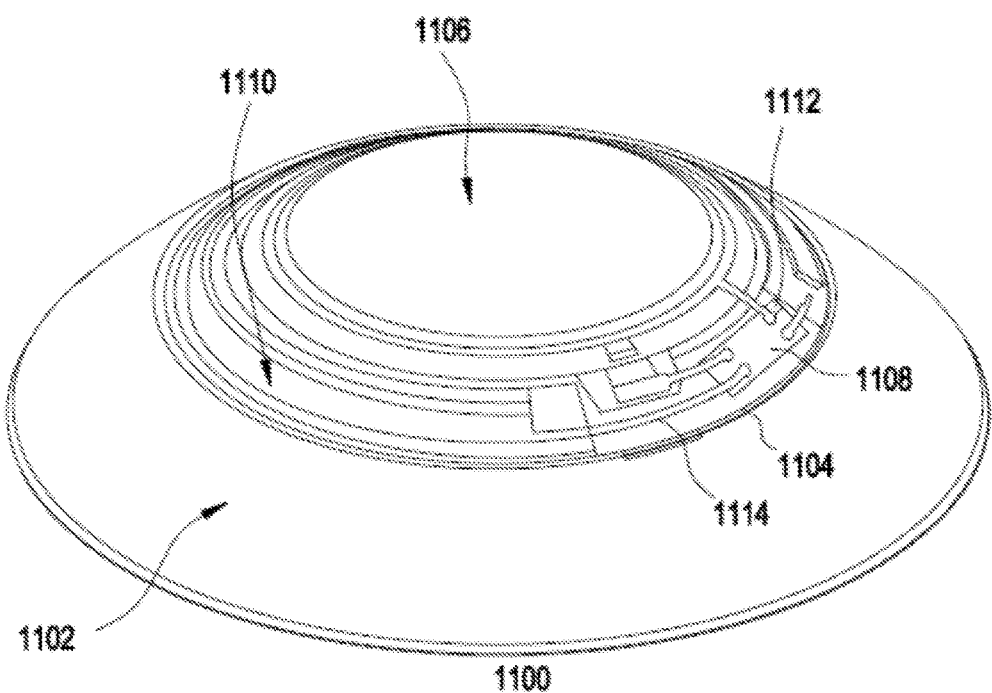
FIG. 11 illustrates a diagrammatic representation of an electronic insert, including a blink detector, for a powered contact lens in accordance with the present invention.

FIG. 11 illustrates a contact lens with an electronic insert comprising a blink detection system in accordance with the present embodiments (invention). The contact lens 1100 comprises a soft plastic portion 1102 which comprises an electronic insert 1104. This insert 1104 includes a lens 1106 which is activated by the electronics, for example focusing near or far depending on activation. Integrated circuit 1108 mounts onto the insert 1104 and connects to batteries 1110, lens 1106, and other components as necessary for the system. The integrated circuit 1108 includes a photosensor 1112 and associated photodetector signal path circuits. The photosensor 1112 faces outward through the lens insert and away from the eye, and is thus able to receive ambient light. The photosensor 1112 may be implemented on the integrated circuit 1108 (as shown) for example as a single photodiode or array of photodiodes. The photosensor 1112 may also be implemented as a separate device mounted on the insert 1104 and connected with wiring traces 1114. When the eyelid closes, the lens insert 1104 including photodetector 1112 is covered, thereby reducing the light level incident on the photodetector 1112. The photodetector 1112 is able to measure the ambient light to determine if the user is blinking or not. Based on this disclosure one of ordinary skill in the art should appreciate that photodetector 112 may be replaced or augmented by the other sensors discussed in this disclosure.

Additional embodiments of the blink detection algorithm may allow for more variation in the duration and spacing of the blink sequence, for example by timing the start of a second blink based on the measured ending time of a first blink rather than by using a fixed template or by widening the mask "don't care" intervals (0 values).

It will be appreciated that the blink detection algorithm and/or sleep detection algorithm may be implemented in digital logic or in software running on a microcontroller. The algorithm logic or microcontroller may be implemented in a single application-specific integrated circuit, ASIC, with photodetection signal path circuitry and a system controller, or it may be partitioned across more than one integrated circuit.

In accordance with another embodiment, a powered or electronic ophthalmic lens may incorporate an eyelid or lid position sensor. It is known that the eyelids protect the globe in a number of ways, including the blink reflex and the tear spreading action. The blink reflex of the eyelids prevents trauma to the globe by rapidly closing upon a perceived threat to the eye. Blinking also spreads tears over the globe's surface to keep it moist and rinse away bacteria and other foreign matter. But the movement of the eyelids may also indicate other actions or functions at play beyond being used to alert and/or track when an individual (or wearer) wearing an electronic ophthalmic lens that he or she is in danger of falling asleep. It is also important to note that the sensed data, in addition to or in alternate use may simply be utilized as part of a collection process rather than as a triggering event. For example, the sensed data may be collected, logged and utilized in treating medical conditions or recording amount of sleep. In other words, it should also be appreciated that a device utilizing such a sensor may not change state in a manner visible to the user; rather the device may simply log data. For example, such a sensor could be used to determine if a user has fallen asleep during a work shift.

Figure 12A:
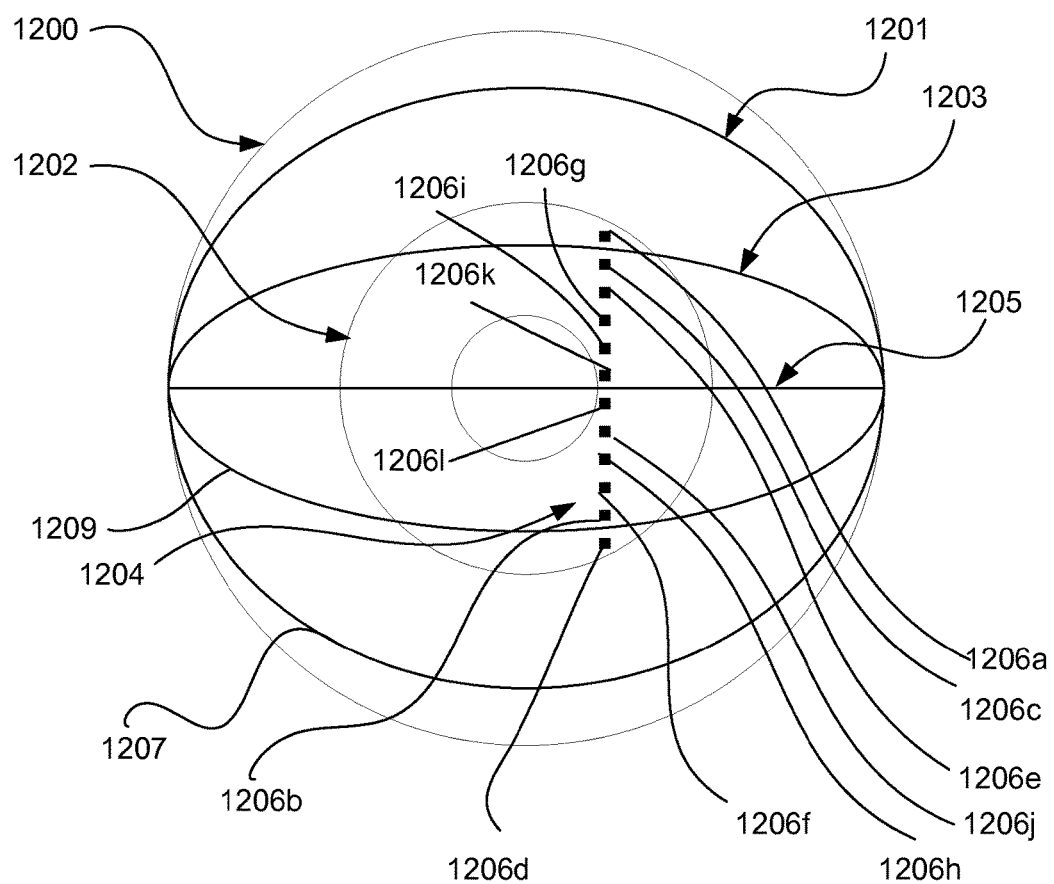
FIGS. 12A and 12B illustrate diagrammatic representations of eyelid position sensors in accordance with the present invention.
Figure 12B:
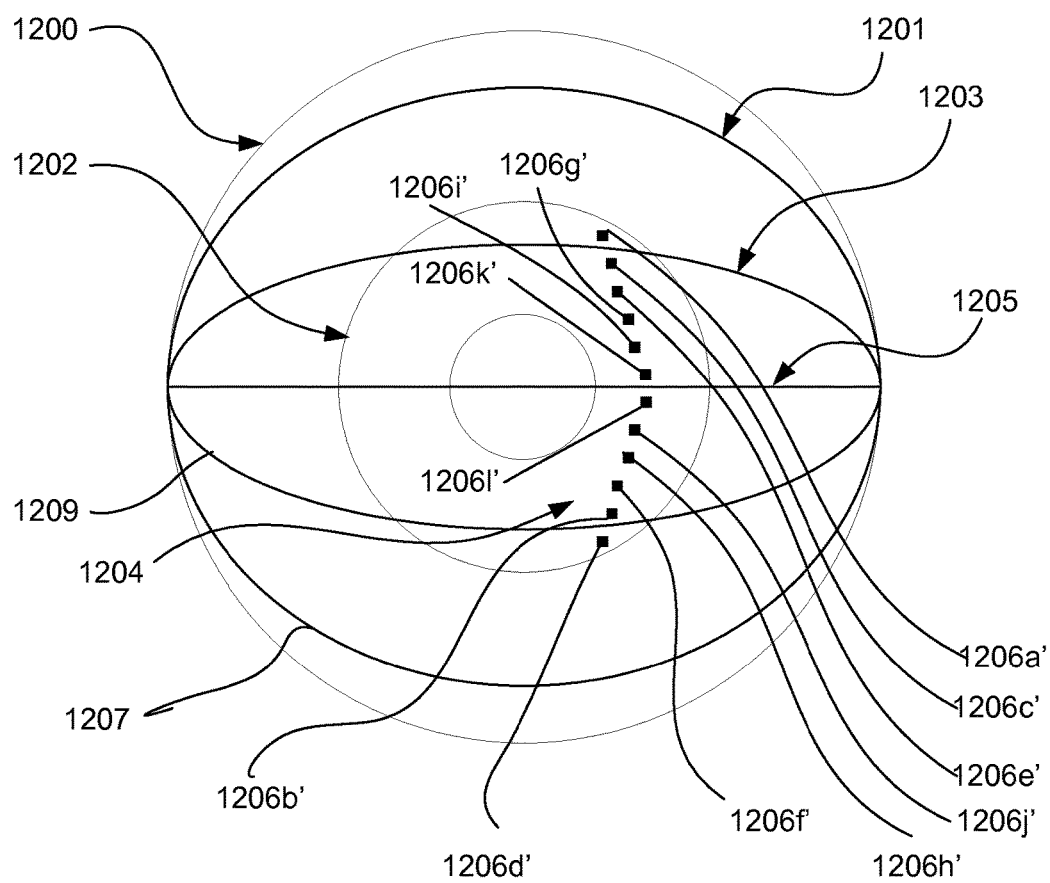

Referring now to FIG. 12A, there is illustrated a lid position sensor system on an eye 1200. The system is incorporated into a contact lens 1202. The top and bottom eyelids are shown, with the top lid having possible locations 1201, 1203, and 1205 in order of increasing closure. The bottom eyelid is also illustrated with levels of closure corresponding to the top lid; namely, locations 1207, 1209 and 1205. When the eyelids are closed, they occupy the same position; namely, 1205. The contact lens 1202 in accordance with the embodiment comprises a sensor array 1204. This sensor array 1204 includes one or more photosensors. In this embodiment, the sensor array 1204 comprises twelve (12) photosensors 1206a-1206l. With the top lid at position 1201 and the bottom lid at position 1207, all photosensors 1206a-1206l are exposed and receive ambient light, thereby creating a photocurrent which may be detected by an electronic circuit described herein. With the lids partially closed at positions 1203 and 1209, the top and bottom photosensors 1206a and 1206b are covered, receive less light than the other photosensors 1206c-1206l, and output a correspondingly lower current which may be detected by the electronic circuit. With the lids totally closed in position 1205, all sensors 1206a-1206l are covered with a corresponding reduction in current. This system may be used to detect lid position by sampling each photosensor in the sensor array and using the photocurrent output versus sensor position to determine lid position, for example, if the upper and lower eyelids do not fully open after blinks indicating potential onset of sleep or fatigue. It will be appreciated that the photosensors should be placed in suitable locations on the contact lens, for example providing enough sample locations to reliably determine lid position while not obstructing the clear optic zone (roughly the area occupied by a dilated pupil.) This system may also be used to detect blinks by routinely sampling the sensors and comparing measurements over time. In an alternative embodiment, photosensors 1206a'-1206l' of a sensor array 1204' form an arcuate pattern around the pupil while being vertically spaced from each other as illustrated, for example, in FIG. 12B. Under either of the illustrated embodiment, one of ordinary skill in the art should appreciate that a number other than 12 may be used in the sensor array. Further examples include a number in a range of 3 through 15 (including the end points in at least one embodiment), and more particularly a number in a range of 4 through 8 (including the end points in at least one embodiment).

Figure 13:
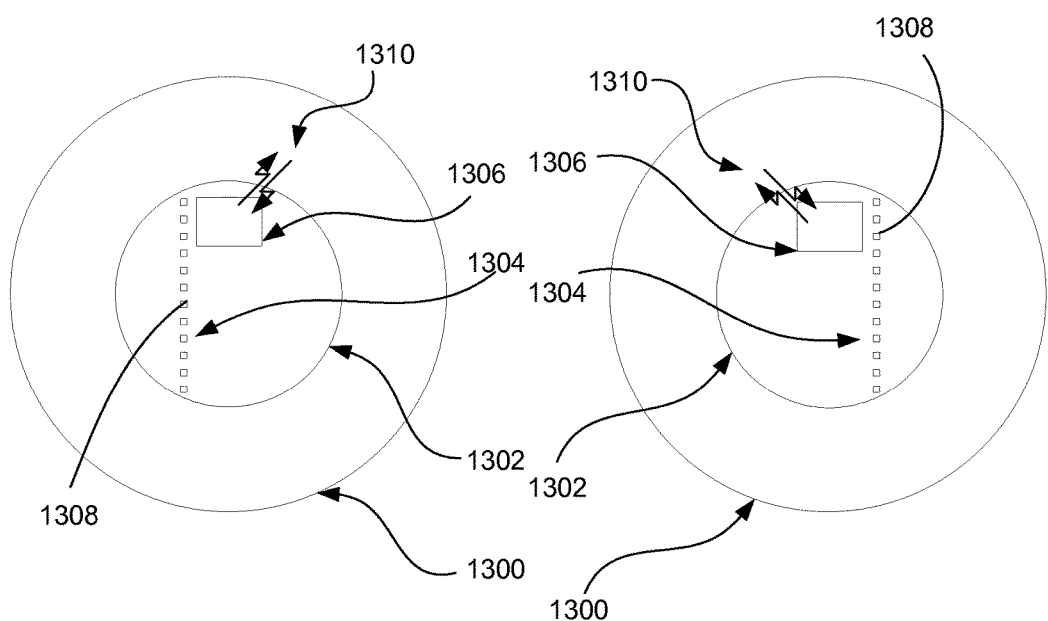
FIG. 13 illustrates a diagrammatic representation of two eyelid position sensors having a communication channel for synchronizing operation between two eyes in accordance with the present invention.

FIG. 13 illustrates a system in which two eyes 1300 are at least partially covered with contact lenses 1302. Sensor arrays 1304 are present in both of the contact lenses 1302 to determine lid position, as previously described with respect to FIG. 12A. In this embodiment, the contact lenses 1302 each comprise an electronic communication component 1306. Electronic communication component 1306 in each contact lens 1302 permits two-way communication to take place between the contact lenses 1302. The electronic communication components 1306 may comprise radio frequency (RF) transceivers, antennas, interface circuitry for photosensors 1308, and associated or similar electronic components. The communication channel represented by line 1310 may comprise RF transmissions at the appropriate frequency and power with an appropriate data protocol to permit effective communication between the contact lenses 1302. Transmission of data between the two contact lenses 1302 may, for example, verify that both lids have closed in order to detect a true, purposeful blink rather than a wink or involuntary blink. The transmission may also allow a system to determine if both eyelids have closed by a similar amount, for example, that which is associated with a user reading up-close. Data transmission may also take place to an external device, for example, spectacle glasses, a patch worn on the user's temple, or a smartphone (or other processor based system). In at least one example, a patch worn by the wearer includes a transducer activated by the alert mechanism to alert the wearer if they have fallen asleep. In at least one embodiment, the electronic communication components allow for the transmission of logged sleep data to the smartphone (or other external device). As such the electronic communication components 1306 may be present on just one lens in at least one alternative embodiment. In an alternative embodiment, an accelerometer present in the smartphone (or other accelerometer equipped device with transmission capability) worn by the individual provides movement data for use in crosschecking a sleep determination such as a lack of general movement is indicative of the possibility of sleep or data indicative of the individual being stationary.

Figure 14A:
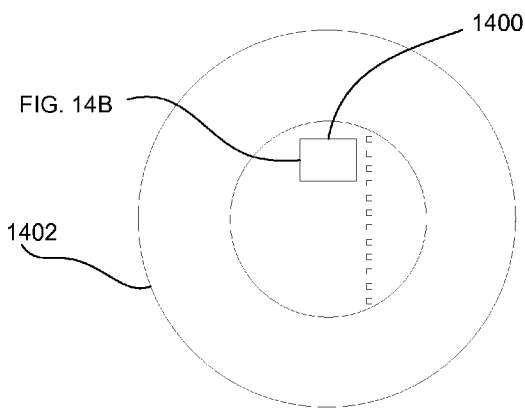
FIG. 14A illustrates a diagrammatic representation of an electronic system incorporated into a contact lens for detecting eyelid position in accordance with the present invention.
Figure 14B:
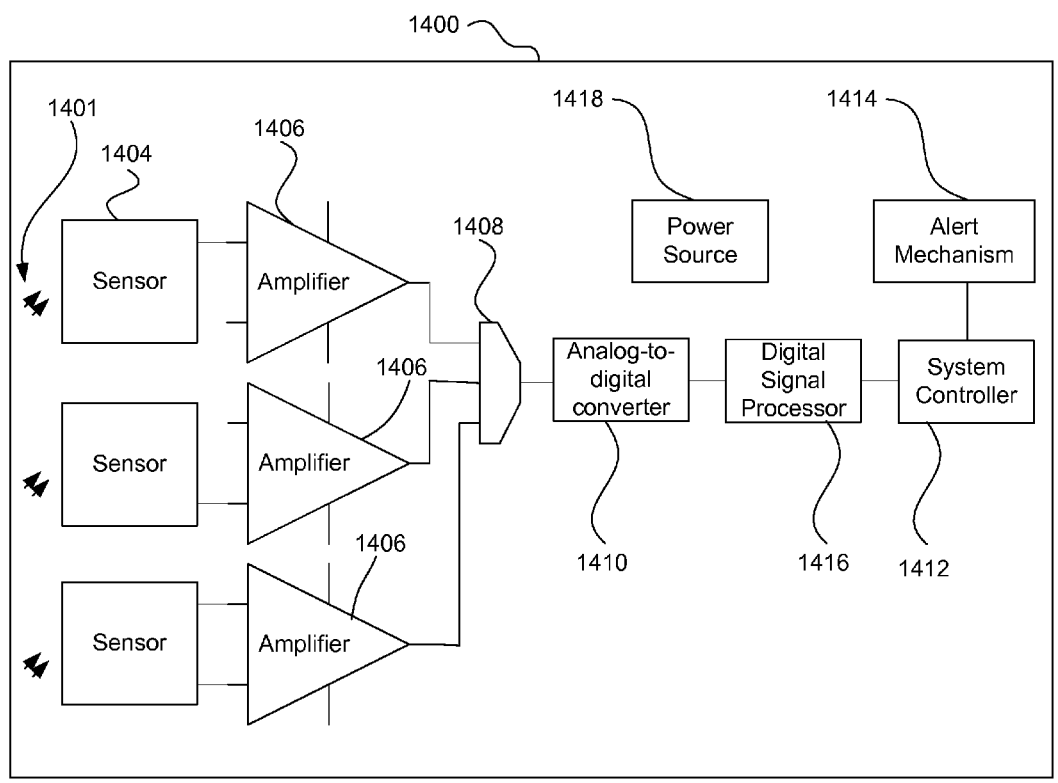
FIG. 14B illustrates an enlarged view of the electronic system of FIG. 14A.

FIGS. 14A and 14B illustrate an electronic system 1400 in which lid position photosensors, as set forth above, are used to trigger activity in a contact lens 1402 or more specifically, a powered or electronic ophthalmic lens. FIG. 14A shows the electronic system 1400 on the lens 1402, and FIG. 14B is an exploded view of the system 1400. Light 1401 is incident onto one or more photosensors 1404 as previously described with respect to FIG. 12. These photosensors 1404 may be implemented with photodiodes, cadmium sulfide (CdS) sensors, or other technologies suitable for converting ambient light into current. Depending on the choice of photosensors 1404, amplifiers 1406 or other suitable circuitry may be required to condition the input signals for use by subsequent or downstream circuits. A multiplexer 1408 permits a single analog-to-digital converter (or ADC) 1410 to accept inputs from multiple photosensors 1404. The multiplexer 1408 may be placed immediately after the photosensors 1404, before the amplifiers 1406, or may not be used depending on considerations for current consumption, die size, and design complexity. Since multiple photosensors 1404 are needed at various positions on the eye to detect lid position, sharing downstream processing components (for example amplifiers, an analog-to-digital converter, and digital signed processors) may significantly reduce the size needed for the electronic circuitry. The amplifiers 1406 create an output proportional to the input, with gain, and may function as transimpedance amplifiers which convert input current into output voltage. The amplifiers 1406 may amplify a signal to a usable level for the remainder of the system, such as giving the signal enough voltage and power to be acquired by the ADC 1410. For example, the amplifiers 1406 may be necessary to drive subsequent blocks since the output of the photosensors 1404 may be quite small and may be used in low-light environments. Amplifiers 1406 may also be implemented as variable-gain amplifiers, the gain of which may be adjusted by a system controller 1412 to maximize the dynamic range of the system 1400. In addition to providing gain, the amplifiers 1406 may include other analog signal conditioning circuitry, such as filtering and other circuitry appropriate to the photosensor 1404 and amplifier 1406 output. The amplifiers 1406 may comprise any suitable device for amplifying and conditioning the signal output by the photosensor 1404. For example, the amplifiers 1404 may simply comprise a single operational amplifier or a more complicated circuit comprising one or more operational amplifiers.

As set forth above, the photosensors 1404 and the amplifiers 1406 are configured to detect incident light 1401 at various positions on the eye and convert the input current into a digital signal usable ultimately by the system controller 1412. The system controller 1412 is preferably pre-programmed to sample each photosensor 1404 on the eye to detect lid position and provide an appropriate output signal to an alert mechanism 1414. The system controller 1412 also comprises associated memory. The system controller 1412 may combine recent samples of the photosensors 1404 to preprogrammed patterns correlating to lid open and squinting positions. For example, when the pattern matches that of both eyelids partially closing associated with fatigue, the system controller 1412 may trigger the alert mechanism 1414 to alert the wearer and/or log data. Recording a user's eyelid patterns under various ambient light and focal distance situations may be required to program the system controller 1412 for reliable detection. The system 1400 may need to differentiate between eyelid position changes, normal changes in ambient light, shadows, and other phenomena. This differentiation may be accomplished through proper selection of the sampling frequency, amplifier gain, and other system parameters, optimization of sensors placement in the contact lens, determination of lid position patterns, recording ambient light, comparing each photosensor to adjacent and all photosensors, and other techniques to discern lid position uniquely.

In this embodiment, the ADC 1410 may be used to convert a continuous, analog signal output from the amplifiers 1406 through the multiplexer into a sampled, digital signal appropriate for further signal processing. For example, the ADC 1410 may convert an analog signal output from the amplifiers 1406 into a digital signal that may be useable by subsequent or downstream circuits, such as a digital signal processing system or microprocessor 1416. A digital signal processing system or digital signal processor 1416 may be utilized for digital signal processing, including one or more of filtering, processing, detecting, and otherwise manipulating/processing sampled data to permit incident light detection for downstream use. The digital signal processor 1416 may be preprogrammed with various lid patterns. The digital signal processor 1416 also comprises associated memory in at least one embodiment. The digital signal processor 1416 may be implemented utilizing analog circuitry, digital circuitry, software, and/or preferably a combination thereof. The ADC 1410 along with the associated amplifiers 1406 and digital signal processor 1416 are activated at a suitable rate in agreement with the sampling rate previously described, for example, every one hundred (100) ms.

A power source 1418 supplies power for numerous components comprising the lid position sensor system 1400. The power source 1418 may also be utilized to supply power to other devices on the contact lens. The power may be supplied from a battery, energy harvester, or other suitable means as is known to one of ordinary skill in the art. Essentially, any type of power source 1418 may be utilized to provide reliable power for all other components of the system. A lid position sensor array pattern, processed from analog to digital, may enable activation of the system controller 1412 or a portion of the system controller 1412. Furthermore, the system controller 1412 may control other aspects of a powered contact lens depending on input from the digital signal processor 1408, for example, activating the alert mechanism 1414.

Figure 15:
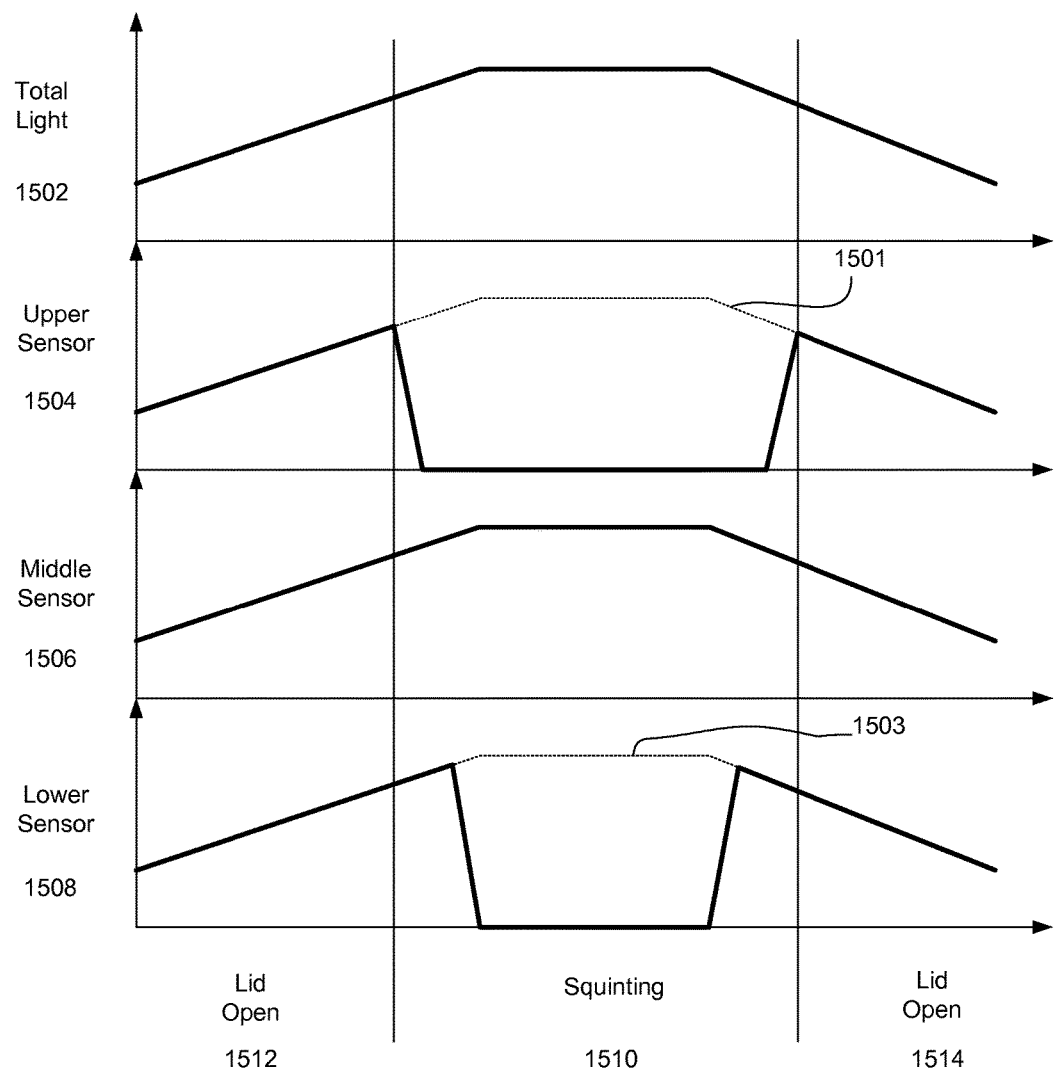
FIG. 15 illustrates a diagrammatic representation of outputs from eyelid position sensors in accordance with the present invention.

Referring now to FIG. 15 there is illustrated an output characteristic for three photosensors positioned at three different vertical positions on the contact lens. The output characteristics may represent the current proportional to incident light on each photosensor or may represent a downstream signal, for example digital sampled data values versus time at the output of the ADC (element 1410 in FIG. 14B). Total incident light 1502 increases, holds steady, then decreases, for example when walking from a dark room to a bright hallway then back to a dark room. All three photosensors 1504, 1506, and 1508 would output a signal similar to that of the ambient light if the eyelid remained open, illustrated by dotted lines 1501 and 1503 for photosensors 1504 and 1508. In addition to the ambient light level 1502 changing, partial closure of the eyelids is indicated by position 1510, different than that of the lid open positions 1512 and 1514. When the lid partially closes, upper photosensor 1504 becomes covered by the upper eyelid and outputs a correspondingly lower level due to obstruction of the photosensor by the eyelid. Despite ambient light 1502 increasing, photosensor 1504 receives less light and outputs a lower signal due to the partially closed eyelid. Similar response is observed with photosensor 1508 which becomes covered. Middle sensor 1506 is not covered during squinting and thus continues to see the light level increase, with a corresponding increase in output level. While this example illustrates one particular case, it should be apparent how various configurations of sensor position and eyelid movement could be detected.

Figure 16A:
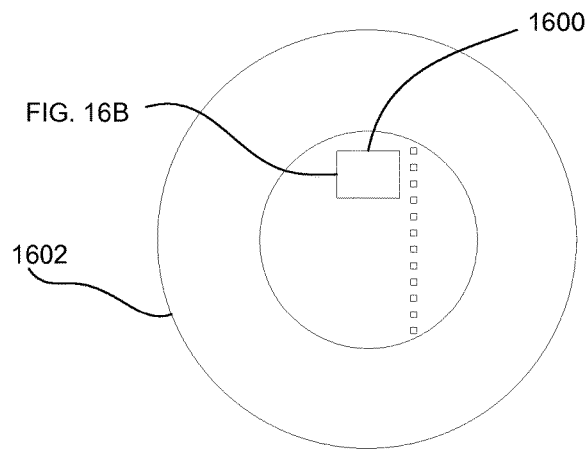
FIG. 16A illustrates a diagrammatic representation of another electronic system incorporated into a contact lens for detecting eyelid position in accordance with the present invention.
Figure 16B:
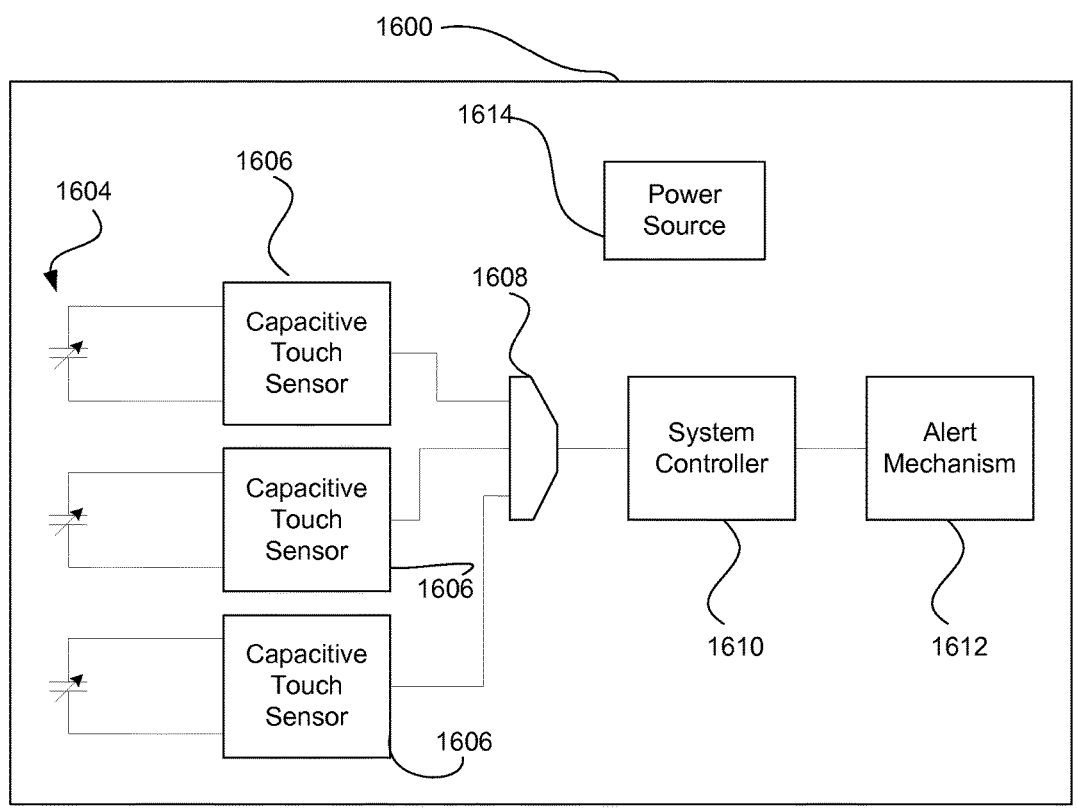
FIG. 16B illustrates an enlarged view of the electronic system of FIG. 16A.

FIGS. 16A and 16B illustrate an alternate detection system 1600 incorporated into a contact lens 1602. Once again FIG. 16A shows the system 1600 on the lens 1602 and FIG. 16B show an exploded view of the system 1600. In this embodiment, capacitive touch sensors 1604 are utilized instead of photosensors. Capacitive touch sensors are common in the electronics industry, for example in touch-screen displays. The basic principle is that a variable capacitor 1604 is implemented in a physical manner such that the capacitance varies with proximity or touch, for example, by implementing a grid covered by a dielectric. Sensor conditioners 1606 create an output signal proportional to the capacitance, for example, by measuring the change in an oscillator comprising the variable capacitor or by sensing the ratio of the variable capacitor to a fixed capacitor with a fixed-frequency AC signal. The output of the sensor conditioners 1606 may be combined with a multiplexer 1608 to reduce downstream circuitry. In this embodiment, the necessary signal conditioning circuitry as described above with respect to FIG. 14 is omitted for simplicity. A system controller 1610 receives inputs from the capacitance sensor conditioner 1606 via the multiplexor 1608, for example, by activating each sensor in order and recording the values. It may then compare measured values to pre-programmed patterns and historical samples to determine lid position. It may then activate a function in an alert mechanism 1612, for example, causing a variable-focus lens to change to a closer focal distance. The capacitor touch sensors 1604 may be laid out in a physical pattern similar to that previously described for the photodetectors, but would be optimized for detecting changes in capacitance with lid position. The sensors, and for that matter the whole electronic system, would be encapsulated and insulated from the saline contact lens environment. As the eyelid covers a sensor 1604, the change in capacitance would be detected rather than the change in ambient light previously described. FIG. 16B also illustrates the inclusion of a power source 1614 in at least one embodiment.

It is important to note that ADC's and digital signal processing circuitry may be utilized in accordance with the capacitive touch sensors if needed as illustrated with respect to the photosensors of FIG. 14B. In an alternative embodiment, the capacitive touch sensors are any pressure sensor. In a further embodiment, there is a combination of photosensors and pressure sensors on the lens.

In one embodiment, the electronics and electronic interconnections are made in the peripheral zone of a contact lens rather than in the optic zone. In accordance with an alternate embodiment, it is important to note that the positioning of the electronics need not be limited to the peripheral zone of the contact lens. All of the electronic components described herein may be fabricated utilizing thin-film technology and/or transparent materials. If these technologies are utilized, the electronic components may be placed in any suitable location as long as they are compatible with the optics.

Figure 17A:
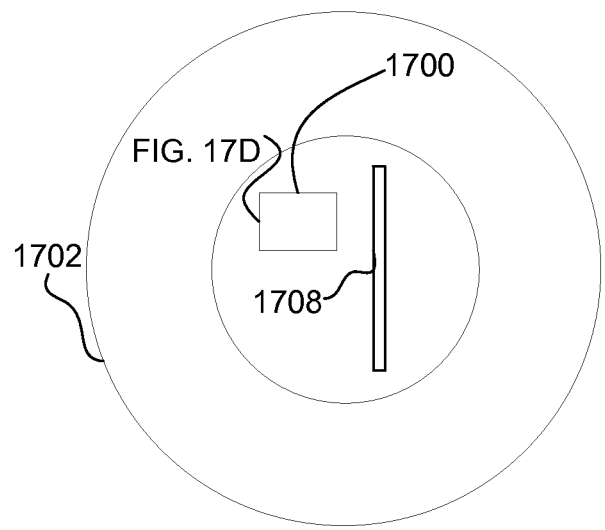
FIG. 17A-17C illustrate diagrammatic representations of an eyelid position detecting system in accordance with the present invention.
Figure 17B:
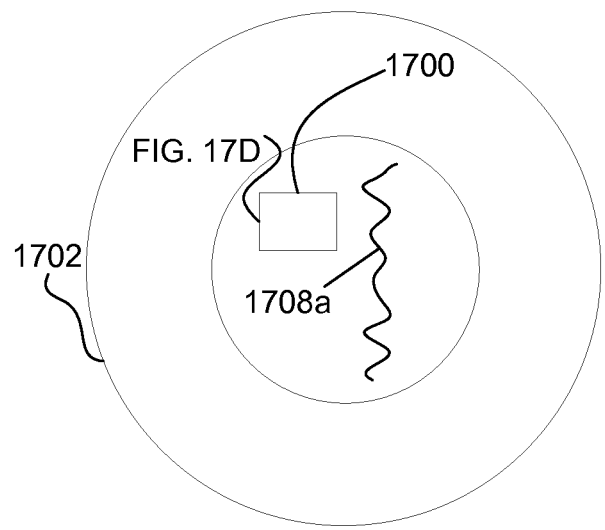
Figure 17C:
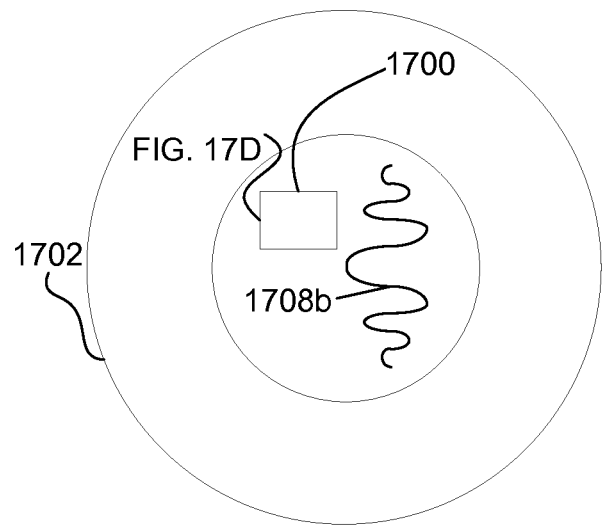
Figure 17D:
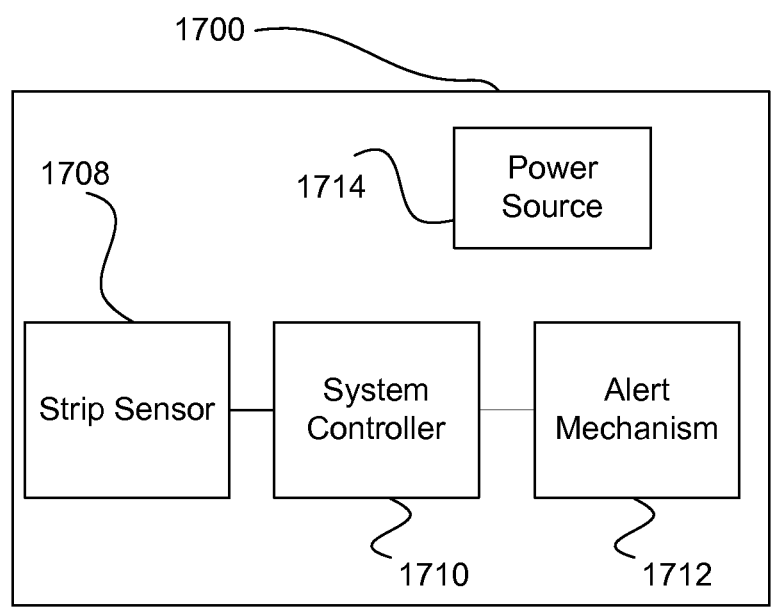
FIG. 17D illustrates an enlarged view of the electronic system of FIGS. 17A-17C.

FIGS. 17A-17D illustrate an alternative embodiment where the lid position sensor system is a sensor having a strip that covers a plurality of vertical points along the contact lens 1702 that works in conjunction with circuit 1700. One example of a sensor that may have a strip configuration is a capacitance sensor. FIG. 17A illustrates an example where the strip 1708 is substantially straight on the contact lens 1702. Although the strip 1708 is illustrated as being orientated parallel to a line bisecting the contact lens 1702, it may have an angled orientation relative to the bisecting line or have an arcuate shape. FIG. 17B illustrates an example where the strip 1708*a* takes a serpentine path along the contact lens 1702. In the embodiment illustrated in FIG. 17C, the serpentine configuration of strip 1708*b* will increase the change in capacitance detected by the circuit 1700 as the eyelids approach a closed state. The level of capacitance change will translate to the amount of eyelid closure. Another example of a sensor that may have a strip configuration is a piezoelectric pressure transducer with a diaphragm and a base having a strip configuration. As the eyelids close, additional pressure will be applied by the eyelids against the piezoelectric pressure transducer thus allowing the ability to determine the level of eyelid closure. The continuous sensing along the vertical axis provides an improved granularity over a plurality of sensors thus providing improved measurement of the eyelid location. FIG. 17D illustrates an electrical circuit that can be used in conjunction with strip sensors 1708, 1708*a*, 1708*b* that includes a system controller 1710, an alert mechanism 1712 and a power source 1714. In a further alternative embodiment, there are multiple strips present. An advantage of an angled and/or serpentine strip configuration is that lid position may still be detected even if the contact lens is orientated incorrectly.

The activities of the digital signal processing block and system controller (1416 and 1412 in FIG. 14B, respectively, system controller 1610 in FIG. 16B, and system controller 1710 in FIG. 17D) depend on the available sensor inputs, the environment, and user reactions. The inputs, reactions, and decision thresholds may be determined from one or more of ophthalmic research, pre-programming, training, and adaptive/learning algorithms. For example, the general characteristics of eyelid movement may be well-documented in literature, applicable to a broad population of users, and pre-programmed into system controller. However, an individual's deviations from the general expected response and/or changes in blink frequency may be recorded in a training session or part of an adaptive/learning algorithm which continues to refine the response in operation of the electronic ophthalmic device. In one embodiment, the user may train the device by activating a handheld fob, which communicates with the device, when the user desires near focus. A learning algorithm in the device may then reference sensor inputs in memory before and after the fob signal to refine internal decision algorithms. This training period could last for one day, after which the device would operate autonomously with only sensor inputs and not require the fob.

Figure 18A:
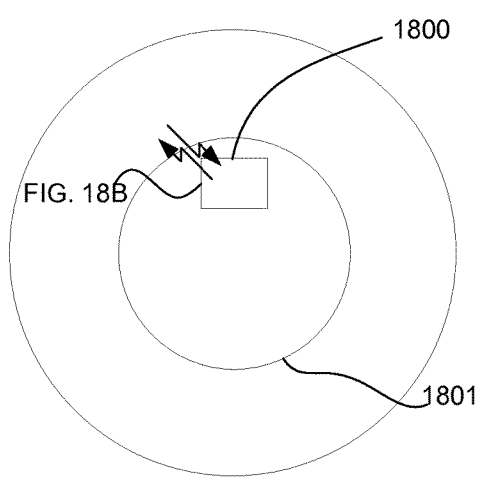
FIG. 18A illustrates a diagrammatic representation of a pupil position and convergence detection system incorporated into a contact lens in accordance with the present invention.
Figure 18C:
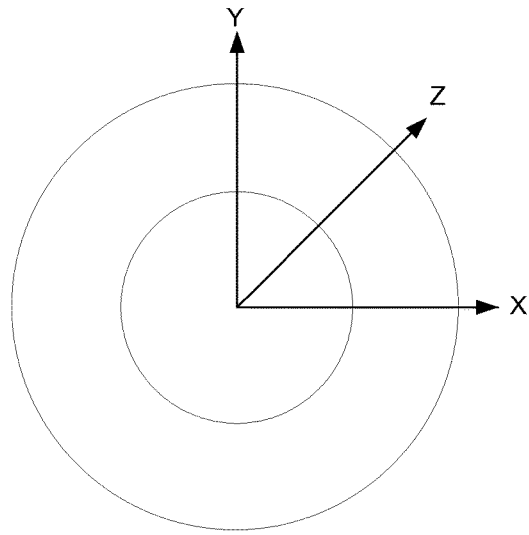
FIG. 18C illustrates an overlay of an X, Y, and Z axes on the eye.
Figure 18B:
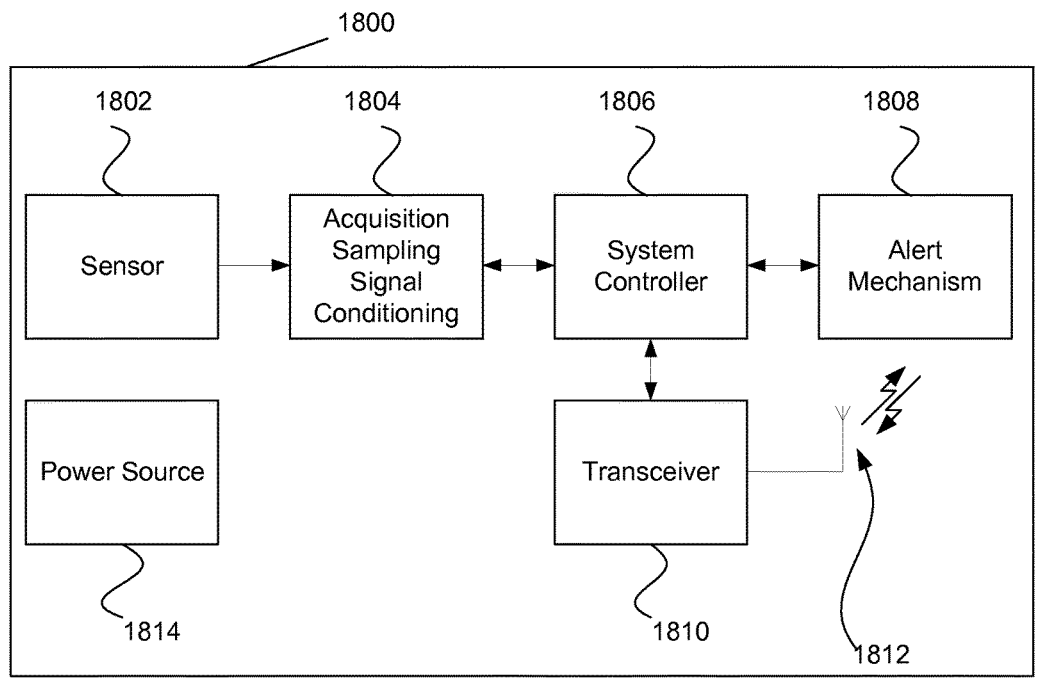
FIG. 18B is an enlarged view of the exemplary pupil position and convergence detection system of FIG. 18A.

FIGS. 18A and 18B are diagrammatic representations of a pupil position and convergence detection system 1800 for control of one or more aspects of a powered ophthalmic lens. Sensor 1802 detects the movement and/or position of the pupil or, more generally, the eye. The sensor 1802 may be implemented as a multi-axis accelerometer on a contact lens 1801. With the contact lens 1801 being affixed to the eye and generally moving with the eye, an accelerometer on the contact lens 1801 may track eye movement. It is important to note that any suitable device may be utilized as the sensor 1802, and more than a single sensor 1802 may be utilized. The output of the sensor 1802 is acquired, sampled, and conditioned by signal processor 1804. The signal processor 1804 may include any number of devices including an amplifier, a transimpedance amplifier, an analog-to-digital converter, a filter, a digital signal processor, and related circuitry to receive data from the sensor 1802 and generate output in a suitable format for the remainder of the components of the system 1800. The signal processor 1804 may be implemented utilizing analog circuitry, digital circuitry, software, and/or a combination thereof. In at least one embodiment, the signal processor 1804 is co-designed with the sensor 1802, for example, circuitry for acquisition and conditioning of an accelerometer are different than the circuitry for a muscle activity sensor or optical pupil tracker. The output of the signal processor 1804 in at least one embodiment is a sampled digital stream and may include absolute or relative position, movement, detected gaze in agreement with convergence, or other data. System controller 1806 receives input from the signal processor 1804 and uses this information, in conjunction with other inputs, to determine whether the wearer is asleep. System controller 1806 may both trigger the activity of sensor 1802 and the signal processor 1804 while receiving output from them. System controller 1806 uses input data from the signal processor 1804 and/or transceiver 1810 to decide if the wearer is lying down based on the orientation of the sensor 1802 based on orientation on an X, Y, and Z axes when no eye movement is detected. If the axes are as illustrated in FIG. 18C, then when the accelerometer detects stable acceleration in the X axis in either direction or in the Z axis in either direction, then the wearer's head has a horizontal orientation. When the accelerometer detects stable acceleration in the Y axis in the negative direction, then the wearer's head is vertical. When the accelerometer detects stable acceleration in the Y and Z axes with or without a stable acceleration in the X axis, then the wearer's head is tilted forward.

FIGS. 18A and 18B illustrate an optional transceiver 1810 receiving and/or transmitting communication through antenna 1812. This communication may come from an adjacent contact lens, spectacle lenses, or other devices. The transceiver 1810 may be configured for two way communication with the system controller 1806. Transceiver 1810 may contain filtering, amplification, detection, and processing circuitry as is common in transceivers. The specific details of the transceiver 1810 are tailored for an electronic or powered contact lens, for example the communication may be at the appropriate frequency, amplitude, and format for reliable communication between eyes, low power consumption, and to meet regulatory requirements. Transceiver 1810 and antenna 1812 may work in the radio frequency (RF) bands, for example 2.4 GHz, or may use light for communication. Information received from transceiver 1810 is input to the system controller 1806, for example, information from an adjacent lens which indicates orientation. The system controller 1806 may also transmit data from, for example the alert mechanism 1808, to the transceiver 1810, which then transmits data over the communication link via antenna 1812.

The system controller 1806 may be implemented as a state machine, on a field-programmable gate array, in a microcontroller, or in any other suitable device. Power for the system 1800 and components described herein is supplied by a power source 1814, which may include a battery, energy harvester, or similar device as is known to one of ordinary skill in the art. The power source 1814 may also be utilized to supply power to other devices on the contact lens 1801.

The pupil position detection system 1800 in at least one embodiment is incorporated and/or otherwise encapsulated and insulated from the saline contact lens 1801 environment.

In at least one embodiment, the lens includes a sensor to detect at least one of removal from a lens storage case and insertion of the lens into the wearer's eye. Examples of sensors that would provide detection include, but are not limited to, a pressure sensor, a reed switch, a salinity sensor, a biosensor and a capacitive sensor. These sensors, in at least one embodiment, work in conjunction with the light sensor to detect the presence of light that occurs after removal of the lens from the storage container. In a further embodiment to the sensor embodiments, the sampling rate used to monitor the sensor may be slowed after the detection of the event being monitored to conserve power while allowing for the detection of removal of the lens from the eye. In an alternative embodiment to the prior embodiment, the sensor would be deactivated upon detection of the lens being placed on the eye.

The pressure sensor may take a variety of forms. One example is a rear-facing pressure sensor connected to the system controller through an analog-to-digital convertor. The rear-facing pressure sensor in at least one embodiment is partially encapsulated in the lens while the analog-to-digital convertor is completely encapsulated in the lens and included as part of any circuit board present in the lens. The system controller resets the accumulator upon receiving a signal from the pressure sensor in excess of an insertion threshold indicating that data collection should begin by the system controller. The system controller sends a signal to the data manager, which in at least one embodiment may be the alert mechanism, to store the current accumulator value when the signal from the pressure sensor then falls below the insertion threshold indicating that the lens has been removed and further data collection is unnecessary. The system controller samples the pressure sensor at a predetermined schedule only when the system controller detects the eyelid is open. Another example of a pressure sensor is a pressure sensor that will detect the removal of pressure from the saline present in the storage container and would provide a signal to activate the other functionality of the lens. A further example of a pressure sensor is a surface acoustic wave resonator with interdigital transducer (IDT). A still further example is a binary contact pressure sensor that either detects pressure or no pressure, but not the level of pressure.

One example of a reed switch completes a circuit in the lens that provides power to the rest of the circuit elements by application of pressure from the wearer's eye upon insertion of the lens or the removal of pressure when the lens is removed from the storage container for use. Upon the respective event occurring, the reed switch would close and complete the circuit to provide an electrical connection between the system controller and the power supply. Another example of a reed switch use is to provide a binary output upon the switch being activated with the binary output providing an indication of the switch being closed (or open depending on the orientation of the switch) as opposed to completing a circuit.

A salinity sensor or biosensor in at least one embodiment would detect salinity or another chemical present in tear fluid. Examples of the substances that could be monitored include, but are not limited to, a pathogen, a biomarker, an active agent, and a chemical. One example of a biosensor is a resistance tab, in electrical communication with system controller, that is capable of binding with the substance being monitored resulting in an increasing resistance as the amount of substance present increases. Another example is a reactive tube(s) that contains a substance, material, or mixture that may react with a specific molecule where a reaction will be indicative of the presence of a chemical being monitored. Yet another example is a biosensor in which a surface is functionalized to have affinity for a certain substance, and an electrical property of the sensor, for example capacitance or voltage, varies in response to the presence of the substance to which the sensor is functionalized. In at least one embodiment, where a chemical being monitored relates to a concentration of some substance in the tear fluid, the reaction may occur directly with that substance or may occur with a separate substance that may indicate concentration of the monitored substance. In other examples, because other electroactive biological components may affect the conductivity within a particular tube, the tube may be lined with or include a selective barrier to minimize interference with the other substances than the substance being monitored. Alternatively to a tube having an increasing conductivity in response to the presence of the monitored substance, the tube may instead have an increasing resistivity in the presence of the monitored substance. A further example will have the hollow tube include material that is selectively permeable or attractive to a specific substance or chemical. Under any of these examples, it may be possible to provide a graduated indication of the level of the substance beyond a binary output.

The capacitive sensor may be rear facing or forward facing. In at least one embodiment, the sensor would be a rear-facing sensor to allow for contact by the wearer's eye. In a further embodiment, once a contact causes a change in capacitance above an insertion threshold indicating that the lens has been inserted, the sensor is deactivated or has its sampling rate decreased. If, however, the sensor was forward facing, then contact by one of the eyelids that would change the capacitance above the insertion threshold would confirm insertion of the lens. In a further embodiment, the forward-facing capacitive sensor would also be used for detection of the position of the eyelids.

In complex systems, which may include multiple sensors, such as powered ophthalmic lenses comprising a number of electronic components, it is preferable to reduce the potential for initiating false actions or false positive triggering when taking action. In accordance with another alternative embodiment, this embodiment is directed to a decision making process and/or voting scheme which utilizes input from multiple sensors to substantially reduce the possibility of changing the state of the powered ophthalmic lens based upon inaccurate, incomplete or erroneous information, changing physiologic conditions, as well as noise and/or interference from internal and external sources. For example, in blink detection, the control system should not determine sleep onset based upon a random blinking pattern due to eye irritation or the like. However, with input from a single sensor or erroneous information from the single sensor or other sensors, incorrect decisions may be made by the system controller. For example, without knowing the pressure applied to the lens, simply closing the eye lids might trigger a sleep determination despite the wearer rubbing their eyes and applying a pressure greater than lid pressure on a pressure sensor(s). In a powered ophthalmic lens comprising a lid position sensor, eyelid movement may also be utilized as a trigger for taking certain actions. For example, when an individual gazes down to focus on a near distance object, the eyelids tend to droop and thus it may be utilized to change the state of the ophthalmic lens. Once again, if only a single input is utilized, a false action may take place due to the fact that the person is sleepy and their eyelids drooped. All of these sensors may be utilized as triggers for action to be implemented by various systems incorporated into an electronic or powered ophthalmic lens, and all of them independently or in limited combination are potentially subject to error. In addition to the sensors already mentioned which are intended to detect certain aspects directly related to determining sleep onset, other sensors may be used to improve state-change sensors by monitoring ambient conditions, noise, and interference. For example, ambient light may be monitored to improve the accuracy of blink detection, lid position, and pupil diameter sensors. Such sensors may be utilized to augment other sensors, for example, by subtracting common mode noise and interference. Sensor inputs may be used to record history readings which are then considered by a complex decision algorithm, for example, one which considers both accelerometer inputs and eye muscle contraction to determine pupil position. Utilizing the voting scheme in accordance with the present invention may reduce the likelihood of error in determining whether the wearer has fallen asleep and may also allow more precise measurements. In other words, for any given action to be taken, there are sensors that may be utilized to check corroborating evidence or to augment input for a given action determined by a primary sensor. It is also important to note that the sensed data, in addition to or in alternate use, may simply be utilized as part of a collection process rather than as a triggering event. For example, the sensed data may be collected, logged and utilized in treating medical conditions. In other words, it should also be appreciated that a device utilizing such a sensor may not change state in a manner visible to the user; rather the device may simply log data.

Figure 19:
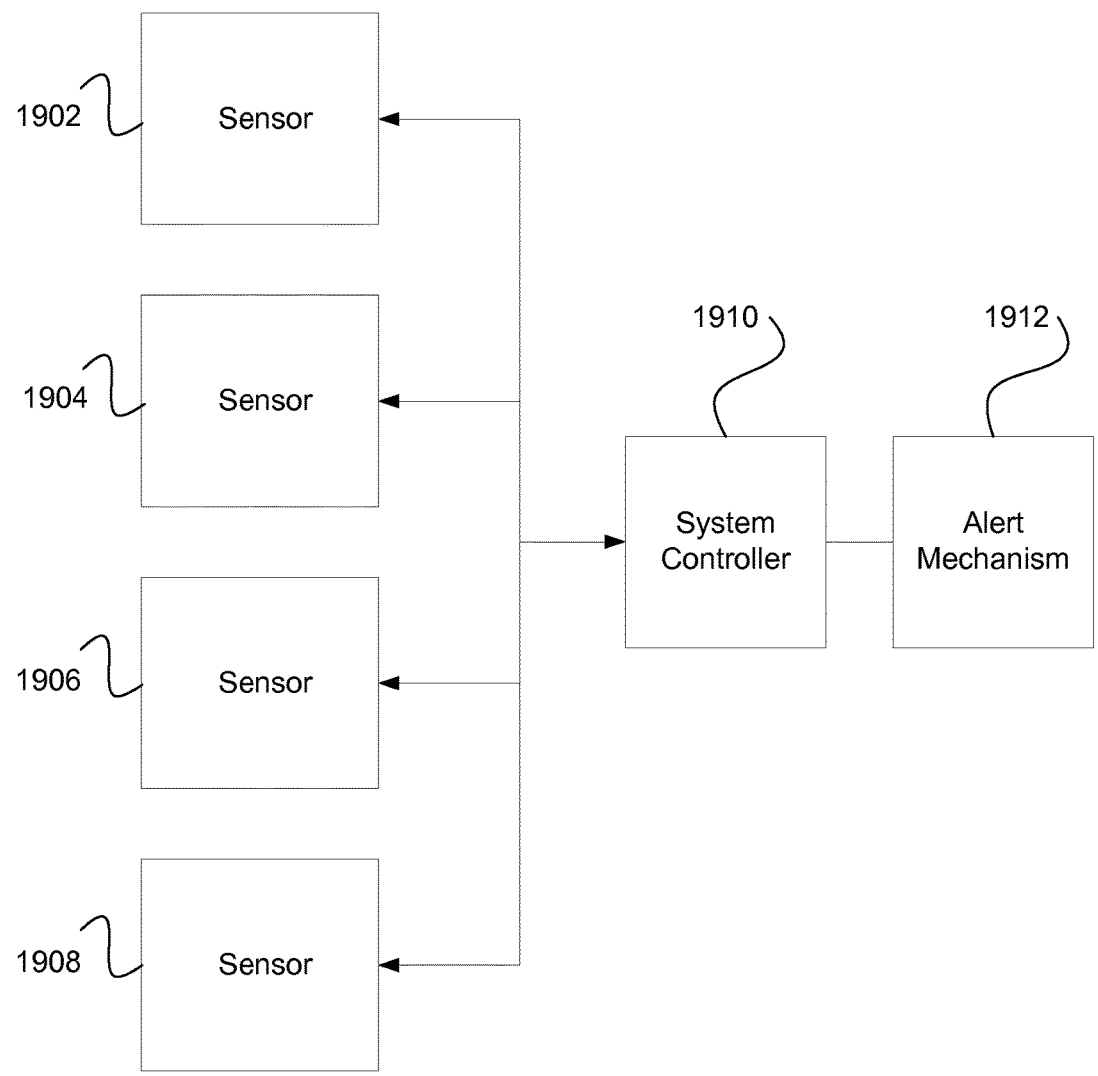
FIG. 19 illustrates a block diagram of a generic system having multiple sensors, a system controller and an alert mechanism, wherein an activation decision is made based on the output of two or more sensors in accordance with the present invention.

Referring now to FIG. 19, there is illustrated a generic system in which sensors 1902, 1904, 1906 and 1908 are used to determine if the state of an alert mechanism 1912 should be changed. The sensors 1902, 1904, 1906 and 1908 may comprise any number of potential inputs including blink action, lid position, pupil position, contact lens orientation, external lens pressure, and the like. The number and type of sensors is determined by the application and user. Each sensor 1902, 1904, 1906 and 1908 may have its own signal conditioning contained within the sensor block, a dedicated block, or within the system controller 1910. The system controller 1910 accepts inputs from each sensor 1902, 1904, 1906 and 1908. It then performs routines to process and compare the input data. Based on these inputs, the system controller 1910 determines if the state of the alert mechanism 1912 should change. For example, the combination of lid droop, low ambient light, and vertical lens orientation may trigger the system controller 1910 to determine the wearer is drowsy and to signal the alert mechanism 1912 to alert the wearer and/or record data. Likewise, the combination of lid closure, vertical orientation for the wearer, and external lid pressure may trigger the system controller 1910 to determine no sleep onset and continue regular operation. The combination of lid closure, horizontal orientation for the wearer may trigger the system controller 1910 to determine sleep onset and to signal the alert mechanism to record data as the sleep is likely intentional sleep given the wearer's orientation. Inputs from various sensors may also be utilized to alter the configuration of the system controller to improve decision making performance, for example, if ambient light decreases, the controller may increase the gain of a photosensor. The system controller may also turn sensors on and/or off, increase and/or decrease sampling rates, and make other changes to the system to optimize performance.

Figure 20:
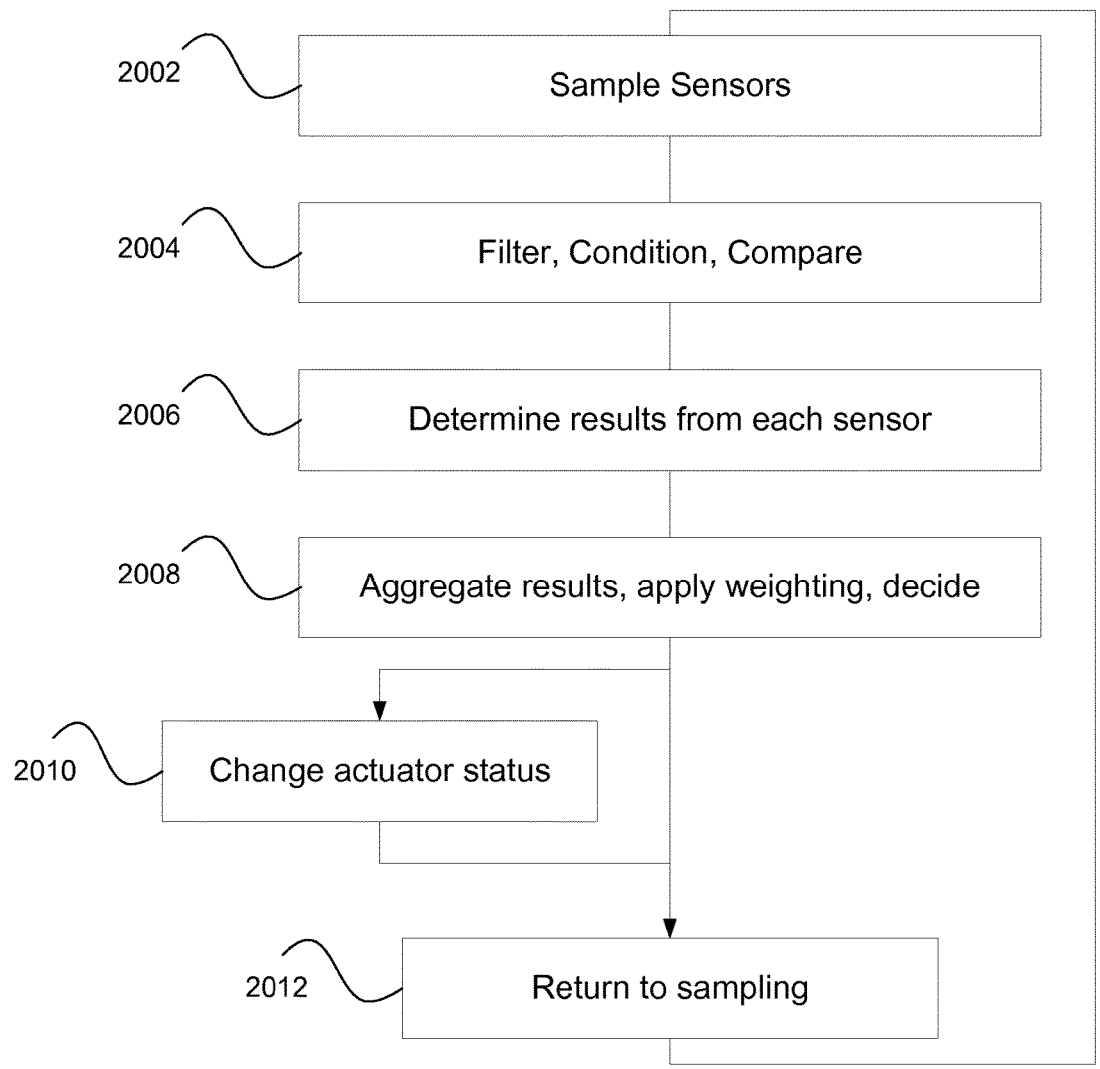
FIG. 20 illustrates a flow chart of a method by which a system controller determines if the state of an alert mechanism is to be changed based upon sensor inputs in accordance with the present invention.

FIG. 20 illustrates a method by which a system controller, for example, system controller 1910 illustrated in FIG. 19, operates to sample sensors and change actuator status and ultimately the state of the powered ophthalmic lens. The first step is to sample the sensors, 2002. This may require triggering other elements to activate, warm-up, calibrate, take readings, condition, and output data. The system controller may also provide configuration information to each sensor based on programmed values and current data, for example, the gain of a photosensor amplifier based on the history of incident light, or these settings may be determined by other elements in the system. Then the method performs filtering and additional conditioning, 2004, for example digital as opposed to analog filtering, along with a comparison to baseline or reference results. One purpose of this step is to properly condition the input data for the next step so that an accurate, repeatable decision may be made. Then the results are determined from each sensor, 2006, for example, the lid position and emitter-detector response. This determination may involve comparison to a pre-programmed or variable threshold, comparison to a specific pattern, or any other determination. The results are aggregated from the previous step, weighting the results and making a decision, 2008. This step in at least one embodiment may involve per-user training and preferences, ensuring all sensors have been sampled before deciding, and various weights applied to the results of each sensor. In at least one embodiment, a decision is made that is predictable and repeatable in the presence of real-world noise and interference. If a decision is made to change the alert mechanism status as described above, then performing this state change at the alert mechanism, 2010. Regardless of the decision regarding state change, returning the system to sampling so another set of measurements and determination may take place, 2012. The total time required to execute the process in FIG. 20 in at least one embodiment is short enough such that the system is responsive to user inputs similar to how individuals naturally interact with their environments. For example, if utilized to activate a variable-power focus lens, the system should change focus state within approximately one (1) second, similar to that of the natural accommodation system.

In an alternative embodiment, the system further includes a memory preservation controller that is in electrical communication with the power source and the system controller. The memory preservation controller, at a predetermined frequency, tests the power source to determine the level of energy that remains. When the remaining energy falls below a predetermined energy threshold, the memory preservation controller sends an instruction to the system controller to no longer sample the sensor system and to send a signal causing the recording by the alert mechanism of the current time and/or accumulator value. The power then is provided to maintain the data in memory and/or data storage present on the lens.

The predetermined energy threshold is based on an estimate of the power required to maintain power supply to any memory or data storage. In a further embodiment, the threshold is adjusted based on the current run time of the lens while still facilitating an estimated period of power for the memory and/or data storage. One example of how to adjust the threshold over time is to decrement a register for each passing of a predetermined time as measured by sampling periods in the lens.

In a further embodiment, the energy level test is done in conjunction with the sampling of the sensor system(s) to compare the energy level of the power source to the threshold under maximum load of the lens as occurs when a sensor system(s) is providing a reading(s). If the energy level for the power source is below a threshold, then there is a high likelihood that an upcoming sensor sampling, prior to the next energy level test, will drain the power source such that the sensor system(s) will provide an incorrect reading because of insufficient power being available and/or stored data will become corrupted thus leading to a data set that is unreliable.

In a modified alternative embodiment, the memory preservation controller places an artificial load on the power source during periods of non-sampling of the sensor(s). Example sampling time periods include but are not limited to 1 minute, 2 minutes, 5 minutes, 10 minutes, 15 minutes, 20 minutes, and 30 minutes. Other examples of testing the power source include, but are not limited to, obtaining a loaded voltage, introducing a special test waveform to pulse current out the battery and measuring voltage drop with the comparison of the results being compared to a predetermined threshold that in a further embodiment can be adjusted downward in view of expected remaining run time.

In a further alternative embodiment, the memory preservation controller monitors the alert mechanism to determine remaining space. When the remaining space is less than a free space threshold, the memory preservation controller sends a signal to the system controller to do at least one of the following: stop sampling the sensor system(s) to avoid creating additional data for storage, send a signal to the data storage to set a flag of memory full and to shift the currently stored data to provide additional space using a first in first out approach, and remove power from the system controller and the sensor system(s) leaving power being supplied to just the data storage.

In a further embodiment to the above embodiments, the memory preservation controller is part of the system controller.

In at least one embodiment, the system further includes a storage box. The storage box includes a housing and a cover that are connected along one edge to facilitate opening the cover relative to the housing to allow for deposit of the contact lens into a cavity in the housing. In alternative embodiments, the storage box may include disinfecting, monitoring, reordering and external connectivity functionality. The disinfecting functionality would allow for the lenses to be used over an extended period of time by the wearer.

In a further embodiment, the storage box includes an antenna such as a RFID antenna for interacting with inserted lenses. The storage box also includes a controller electrically communicating with said antenna and at least one memory, which in at least one embodiment is flash memory like that used in a memory stick. Examples of the interaction include wireless recharging of the power source on one or both lenses, transferring data stored on the lens(es) to memory in (or in communication with) the storage box, and transferring templates and masks based on wearer-specific characteristics from the storage box to at least one lens.

In at least one embodiment, the processor is configured to translate and/or format the data received from the at least one lens to change the time stamp information into actual times based on the current accumulator reading at the time of data transfer as correlated to the current time on the storage box. In an alternative embodiment, the storage box sends a signal to the lens to reset the accumulator to zero and the processor records in memory the time that the accumulator was reset to zero. After reinsertion of the lens into the storage box, the processor notes the current time and determines the number of sampling cycles. In the embodiments where the sampling cycles are of different lengths depending on what is being sampled and/or operational state of the lens(es) since removal of the lens(es), the storage box normalizes the sample periods over the time difference between removal of the lens(es) from the storage box and return of the lens(es) to the storage box as measured by the storage box.

Figure 21:
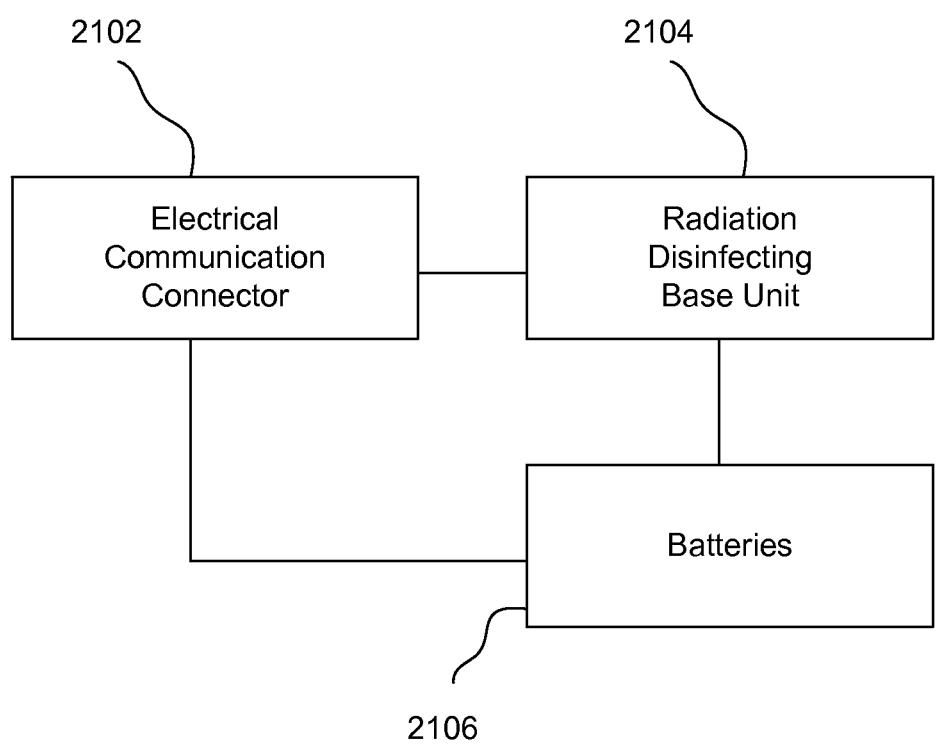
FIG. 21 illustrates a block diagram of a storage box in accordance with at least one embodiment of the present invention.

In a further embodiment, the storage box illustrated in FIG. 21 includes an electrical communication connector 2102 in communication with a radiation disinfecting base unit 2104 contained within a housing such as the previously described housing and cover. The electrical communication connector 2102 may include a universal serial bus (USB) connector or other type of connector. The connector may include a terminal for transferring one or both of data and electrical power. In some embodiments, the electrical communication connector 2102 provides power to operate the radiation disinfecting base unit 2104. Some embodiments may also include one or more batteries 2106 or other power storage device. In some embodiments, the batteries 2106 include one or more lithium-ion batteries or other rechargeable device. The power storage devices may receive a charging electrical current via the electrical communication connector 2102. In at least one battery embodiment, the radiation disinfecting base unit 2104 is operational via stored power in the batteries 2106.

In some embodiments, the electrical communication connector 2102 may include a simple source of AC or DC current.

It should be appreciated that each sensor input may vary for reasons other than changes in the desired focal length. For example, the eye impedance may vary over time due to changes in body hydration, salt intake, level of exertion, or other means. Likewise, pupil diameter may vary due to changes in ambient light levels. Thus, it should be apparent that combining multiple sensor inputs reduces the chances of false positive triggering by requiring more than one input to correlate with a desired change in focal length or by using certain sensor inputs to augment other sensors.

It should also be apparent that the thresholds for each sensor and the combination of sensors used to determine a change in state depends on many variables such as safety, response time, and user preferences. The specific programming of the voting scheme may be based on clinical observations of a number of subjects and individual programming tailored to a specific user. Parameters in the voting scheme may be dependent on sensor inputs, for example, the threshold and gain setting for blink detection may vary with ambient light.

An intraocular lens or IOL is a lens that is implanted in the eye and replaces the crystalline lens. It may be utilized for individuals with cataracts or simply to treat various refractive errors. An IOL typically comprises a small plastic lens with plastic side struts called haptics to hold the lens in position within the capsular bag in the eye. Any of the electronics and/or components described herein may be incorporated into IOLs in a manner similar to that of contact lenses.

Although shown and described in what is believed to be the most practical embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A powered ophthalmic lens, the powered ophthalmic lens comprising:
 a contact lens;
 a power source incorporated into the contact lens;
 an eyelid position sensor system incorporated into the contact lens, the eyelid position sensor system including a sensor array having a plurality of individual sensors vertically spaced from each other to detect eyelid position;
 an accelerometer incorporated into the contact lens for determining head movement;
 a rear facing pressure sensor incorporated into the contact lens configured to determine when the contact lens is on eye;
 a pupil position system having at least one accelerometer for tracking eye movement;
 a system controller configured to sample each individual sensor in the sensor array to detect eyelid position, the accelerometer to detect head movement and the rear facing pressure sensor to detect when the contact lens is on eye, and provide an output control signal, the system controller, the eyelid position sensor system, the accelerometer, the rear facing pressure sensor and the pupil position sensor being configured to determine at least one of whether the contact lens is on eye, tracking length of blink period width and eyelid open period width, level of eyelid droop, eyelid speed, saccades movement of the pupil, or head droop in combination with longer blink period width, the output control signal being indicative of wakefulness;
 at least one alert mechanism configured to receive the output control signal and capable of at least one of providing an alert and storing data in response to a determination by the system controller that the eyelid has been closed for a period of time, a level of eyelid droop, eyelid speed, saccades movement of the pupil, or head droop in combination with longer blink period width indicative of at least one of onset of sleep and drowsiness; and
 a memory preservation controller for testing the power source, at a predetermined frequency, to determine a level of energy that remains, wherein if the energy falls below a predetermined threshold, the memory preservation controller sends an instruction to the system controller to no longer sample the eyelid position sensor system and pupil position system and preserve all data collected.

2. The powered ophthalmic lens according to claim 1, wherein the alert mechanism comprises a light source positioned on the lens to provide a light onto at least one of a retina of a wearer of the lens and the lens itself as the alert.

3. The powered ophthalmic lens according to claim 1, wherein the alert mechanism comprises a transducer to vibrate an eye of a wearer of the lens as the alert.

4. The powered ophthalmic lens according to claim 1, wherein the alert mechanism comprises an electrical stimulator configured to stimulate at least one of a corneal surface and at least one sensory nerve of a cornea.

5. The powered ophthalmic lens according to claim 1, wherein the alert mechanism provides optic zone modification of an optic zone of the contact lens.

6. The powered ophthalmic lens according to claim 1, further comprising at least one electronic communication component in communication with the alert mechanism and configured to transmit a notification to an external device in response to the alert received from the alert mechanism.

7. The powered ophthalmic lens according to claim 1, further comprising a clock, and
wherein the alert mechanism comprises associated memory for storing an initiation of sleep in response to the determination of onset of sleep by the system controller and a termination of sleep in response to a determination of a wearer waking up by the system controller, the alert mechanism configured to store a time stamp from the clock with the initiation of sleep and the termination of sleep.

8. The powered ophthalmic lens according to claim 7, further comprising at least one electronic communication component connected to the memory and the clock, and the at least one electronic communication component configured to retrieve data from the memory and a time stamp from the clock in response to an external inquiry for the stored data.

9. The powered ophthalmic lens according to claim 1, wherein the system controller operates in one of at least two states based on a state input received by the system controller, where the at least two states include an awake operation state and an asleep operation state and the at least two states control the operation of the at least one alert mechanism as to whether the alert is provided based on the detection of onset of sleep by the system controller.

10. The powered ophthalmic lens according to claim 1, wherein
the plurality of individual sensors comprise photosensors for detecting light incident on the eye; and
the eyelid position sensor system further comprises
a multiplexer configured to receive multiple inputs from the photosensors and output a single signal,
an analog-to-digital converter configured to convert the analog signal from the amplifier to a sampled, digital signal for further signal processing, and
a digital signal processor configured to receive an output from the analog-to-digital converter and perform digital signal processing, including one or more of filtering, processing and detecting sampled data to permit incident light detection for downstream use.

11. The powered ophthalmic lens according to claim 10, wherein the digital signal processor comprises associated memory storing two sets of blink templates and blink masks for use by the digital signal processor based on operational state of the lens as determined in response to wearer instructions.

12. The powered ophthalmic lens according to claim 1, wherein the plurality of individual sensors comprise capacitive touch sensors for detecting contact or proximity and outputting a signal indicative thereof; and
the sensor system further comprises sensor conditioners that output a signal proportional to capacitance for downstream use.

13. The powered ophthalmic lens according to claim 12, wherein the eyelid position sensor system further comprises a multiplexer configured to receive multiple inputs from the sensor conductors and output a single signal to the system controller.

14. The powered ophthalmic lens according to claim 1, wherein the eyelid position sensor system further comprises a communication channel for coordinating action between pairs of powered contact lenses.

15. A powered ophthalmic lens, the powered ophthalmic lens comprising:
a contact lens;
a power source incorporated into the contact lens;
an eyelid position sensor system incorporated into the contact lens, the eyelid position sensor system including at least one sensor strip having a plurality of vertical points along its length to detect eyelid position;
an accelerometer incorporated into the contact lens for determining head movement;
a rear facing pressure sensor incorporated into the contact lens configured to determine when the contact lens is on eye;
a pupil position system having at least one accelerometer for tracking eye movement;
a system controller configured to sample each individual sensor in the sensor array to detect eyelid position, the accelerometer to detect head movement and the rear facing pressure sensor to detect when the contact lens is on eye, and provide an output control signal, the system controller, the eyelid position sensor system, the accelerometer, the rear facing pressure sensor and the pupil position sensor being configured to determine at least one of whether the contact lens is on eye, tracking length of blink period width and eyelid open period width, level of eyelid droop, eyelid speed, saccades movement of the pupil, or head droop in combination with longer blink period width, the output control signal being indicative of wakefulness;
at least one alert mechanism configured to receive the output control signal and capable of at least one of providing an alert and storing data in response to a determination by the system controller that the eyelid has been closed for a period of, a level of eyelid droop, eyelid speed, saccades movement of the pupil, or head droop in combination with longer blink period width indicative of at least one of onset of sleep and drowsiness; and
a memory preservation controller for testing the power source, at a predetermined frequency, to determine a level of energy that remains, wherein if the energy falls below a predetermined threshold, the memory preservation controller sends an instruction to the system controller to no longer sample the eyelid position sensor system and pupil position system and preserve all data collected.

16. The powered ophthalmic lens according to claim 15, wherein the alert mechanism comprises at least one of the following:
- a light source positioned on the lens to provide a light onto at least one of a retina of a wearer of the lens and the lens itself as the alert,
- a transducer to vibrate an eye of a wearer of the lens as the alert,
- an electrical simulator configured to stimulate at least one of a corneal surface and at least one sensory nerve of a cornea, and
- a transducer that provides optic zone modification of an optic zone of the contact lens.

17. The powered ophthalmic lens according to claim 15, further comprising a clock, and
- wherein the alert mechanism comprises associated memory for storing an initiation of sleep in response to the determination of onset of sleep by the system controller and a termination of sleep in response to a determination of a wearer waking up by the system controller, the alert mechanism configured to store a time stamp from the clock with the initiation of sleep and the termination of sleep.

\* \* \* \* \*